(12) United States Patent
Shaw et al.

(10) Patent No.: US 6,572,584 B1
(45) Date of Patent: Jun. 3, 2003

(54) RETRACTABLE SYRINGE WITH REDUCED RETRACTION FORCE

(75) Inventors: Thomas J. Shaw, Little Elm, TX (US); Judy Zhu, Plano, TX (US); Diane Rutherford, Corinth, TX (US)

(73) Assignee: Retractable Technologies, Inc., Little Elm, TX (US)

( * ) Notice: Subject to any disclaimer, the term of this patent is extended or adjusted under 35 U.S.C. 154(b) by 0 days.

(21) Appl. No.: 09/633,657

(22) Filed: Aug. 7, 2000

(51) Int. Cl.[7] .................................................. A61M 5/00
(52) U.S. Cl. ......................................... 604/110; 604/195
(58) Field of Search ................................. 604/110, 229, 604/230, 239, 240, 264, 187, 195, 218

(56) References Cited

U.S. PATENT DOCUMENTS

| | | |
|---|---|---|
| 3,306,290 A | 2/1967 | Weltman |
| 4,747,831 A | 5/1988 | Kulli |
| 4,838,863 A | 6/1989 | Allard et al. |
| 4,838,869 A | 6/1989 | Allard |
| 4,841,985 A | 6/1989 | Wanamaker |
| 4,874,382 A | 10/1989 | Lindemann et al. |
| 4,904,242 A | 2/1990 | Kulli |
| 4,955,870 A | 9/1990 | Ridderheim et al. |
| 4,994,034 A | 2/1991 | Botich et al. |
| 5,019,044 A | 5/1991 | Tsao |
| 5,046,508 A | 9/1991 | Weissler |
| 5,049,133 A | 9/1991 | Villen Pascual |
| 5,053,010 A | 10/1991 | McGary et al. |
| 5,064,419 A | 11/1991 | Gaarde |
| 5,084,018 A | 1/1992 | Tsao |
| 5,084,029 A | 1/1992 | Tagliaferri et al. |
| 5,090,962 A | 2/1992 | Landry, Jr. et al. |
| 5,092,853 A | 3/1992 | Courvertier, II |
| 5,112,316 A | 5/1992 | Venturini |
| 5,114,410 A | 5/1992 | Caralt Batlle |
| 5,120,310 A | 6/1992 | Shaw |
| 5,163,918 A | 11/1992 | Righi et al. |
| 5,180,369 A | 1/1993 | Dysarz |
| 5,180,370 A | 1/1993 | Gillespie |
| 5,188,599 A | 2/1993 | Botich et al. |
| 5,201,710 A | 4/1993 | Caselli |
| 5,211,629 A | 5/1993 | Pressly et al. |
| 5,304,138 A | 4/1994 | Mercado |
| 5,324,265 A | 6/1994 | Murray et al. |

(List continued on next page.)

FOREIGN PATENT DOCUMENTS

| | | |
|---|---|---|
| GB | 2 197 792 A | 6/1988 |
| JP | 146773 | 5/2000 |
| WO | WO 95/08358 | 3/1995 |
| WO | WO 96/35463 | 11/1996 |
| WO | WO 98/48869 | 11/1998 |

OTHER PUBLICATIONS

"Disappearing Needle", Designer News, p. 58, Mar. 22, 1993.

*Primary Examiner*—Kevin C. Sirmons
(74) *Attorney, Agent, or Firm*—Locke Liddell & Sapp LLP; Monty L. Ross

(57) ABSTRACT

A tamperproof retractable non-reusable syringe has a one piece hollow outer body with a barrel for a slidable plunger, a transition zone and a smaller diameter nose portion. An elongated needle holder and spring combination is installable from the rear of the outer body, guided into the nose portion and held by cooperating inwardly and outwardly facing surfaces oriented in the direction of retraction at the most constricted part of the transition zone where the nose begins. The plunger has an opening with a dislodgable stopper for receiving parts of the retraction mechanism. The stopper and the head of the needle holder are of significantly reduced diameter from the injection fluid chamber to resist blowing out prematurely. In one embodiment the head of the needle holder is surrounded by a separable retainer member which is slidingly removed by contact with the tip of the plunger after the stopper is mostly or fully removed to avoid cumulation of force required for retraction after the injection.

28 Claims, 13 Drawing Sheets

U.S. PATENT DOCUMENTS

| | | |
|---|---|---|
| 5,346,480 A | 9/1994 | Hess et al. |
| 5,370,620 A | 12/1994 | Shonfeld |
| 5,376,080 A | 12/1994 | Petrussa |
| 5,385,551 A | 1/1995 | Shaw |
| 5,389,076 A | 2/1995 | Shaw |
| 5,407,431 A | 4/1995 | Botich et al. |
| 5,411,489 A | 5/1995 | Pagay et al. |
| 5,423,758 A | 6/1995 | Shaw |
| 5,505,703 A | 4/1996 | Bartlett et al. |
| 5,527,286 A | 6/1996 | Lekhgolts et al. |
| 5,578,011 A | 11/1996 | Shaw |
| 5,613,952 A | 3/1997 | Pressley, Sr. et al. |
| 5,632,733 A | 5/1997 | Shaw |
| 5,800,403 A | 9/1998 | Pressly, Sr. et al. |
| 5,810,775 A | 9/1998 | Shaw |
| 5,997,512 A | 12/1999 | Shaw |
| 6,015,438 A | 1/2000 | Shaw |
| 6,090,077 A | 7/2000 | Shaw |

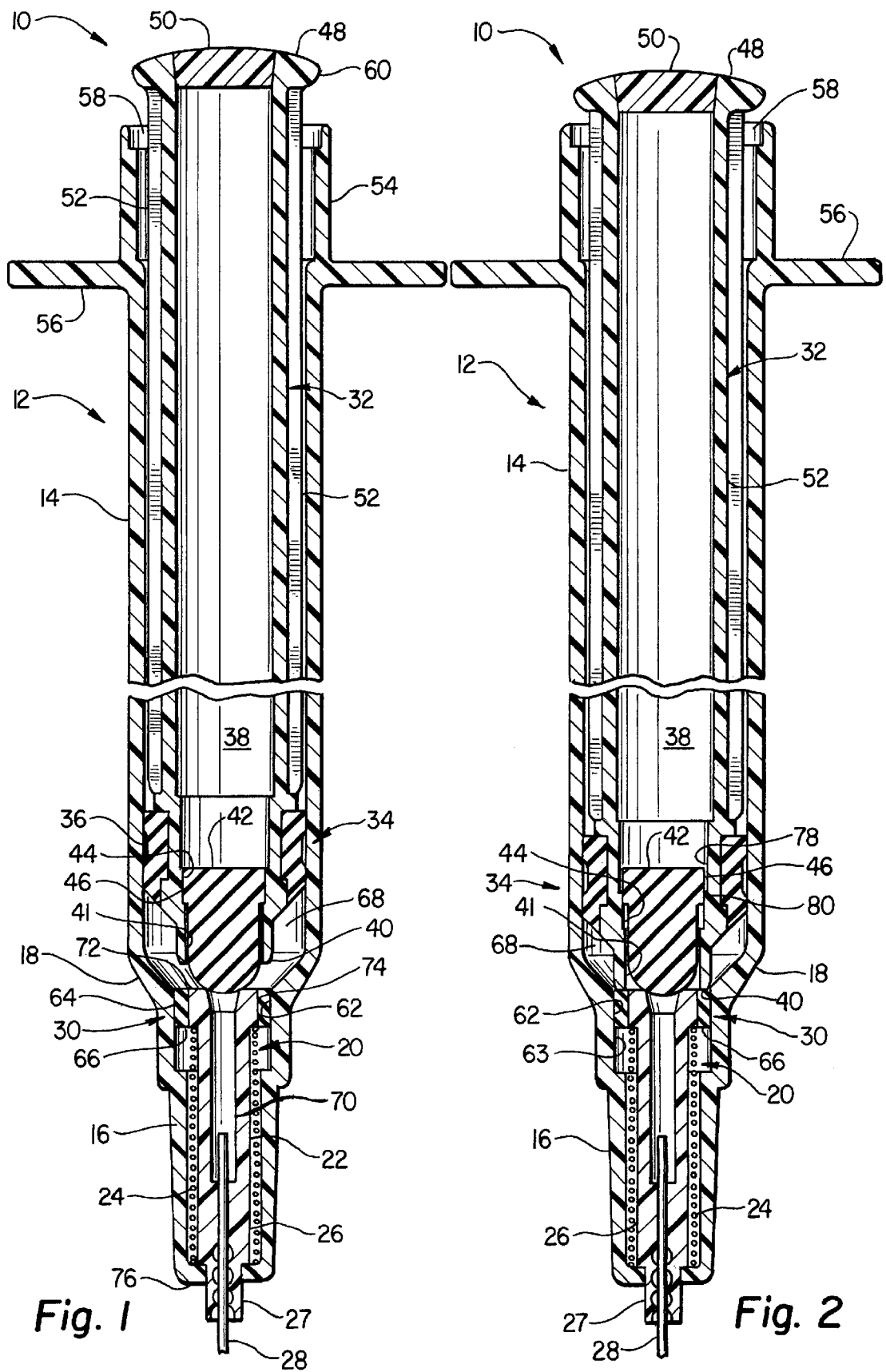

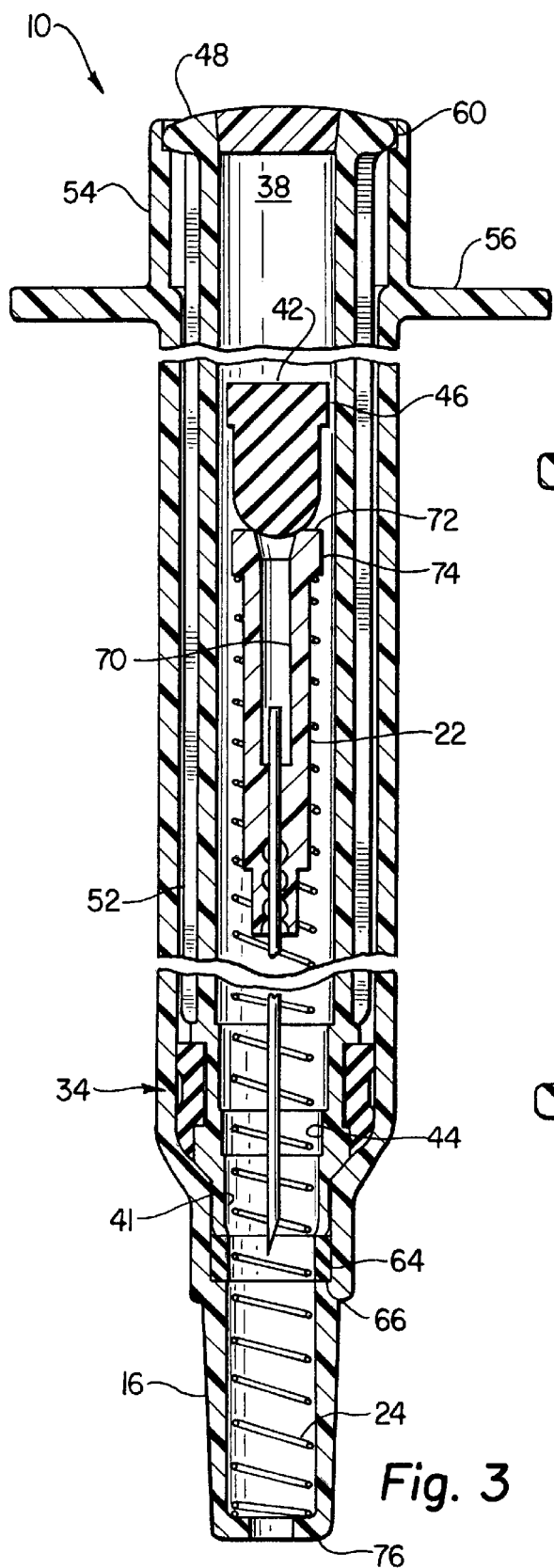
Fig. 3
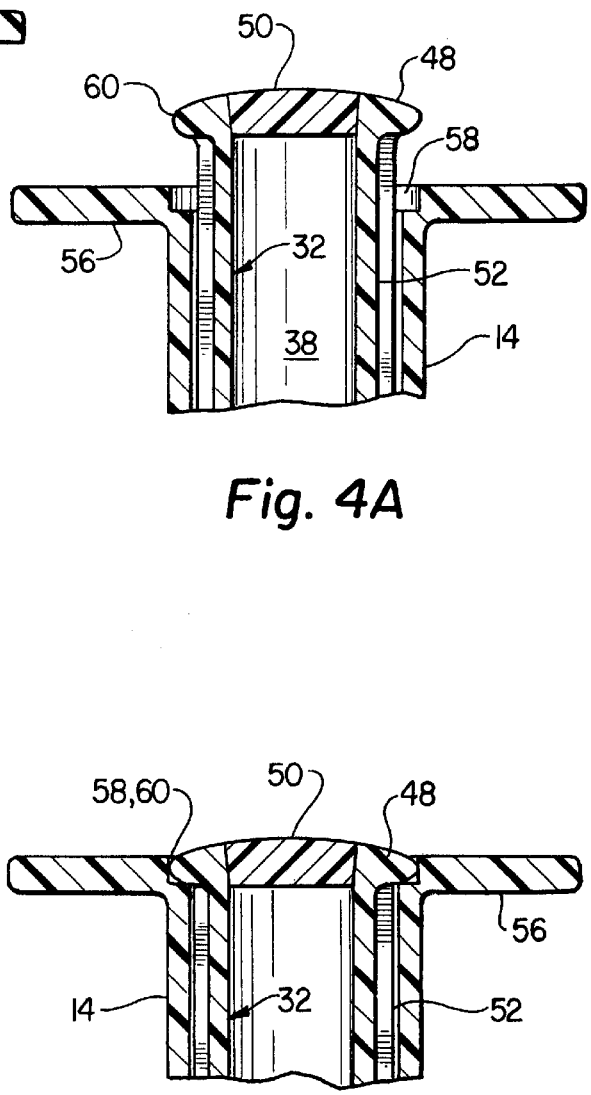
Fig. 4A
Fig. 4B

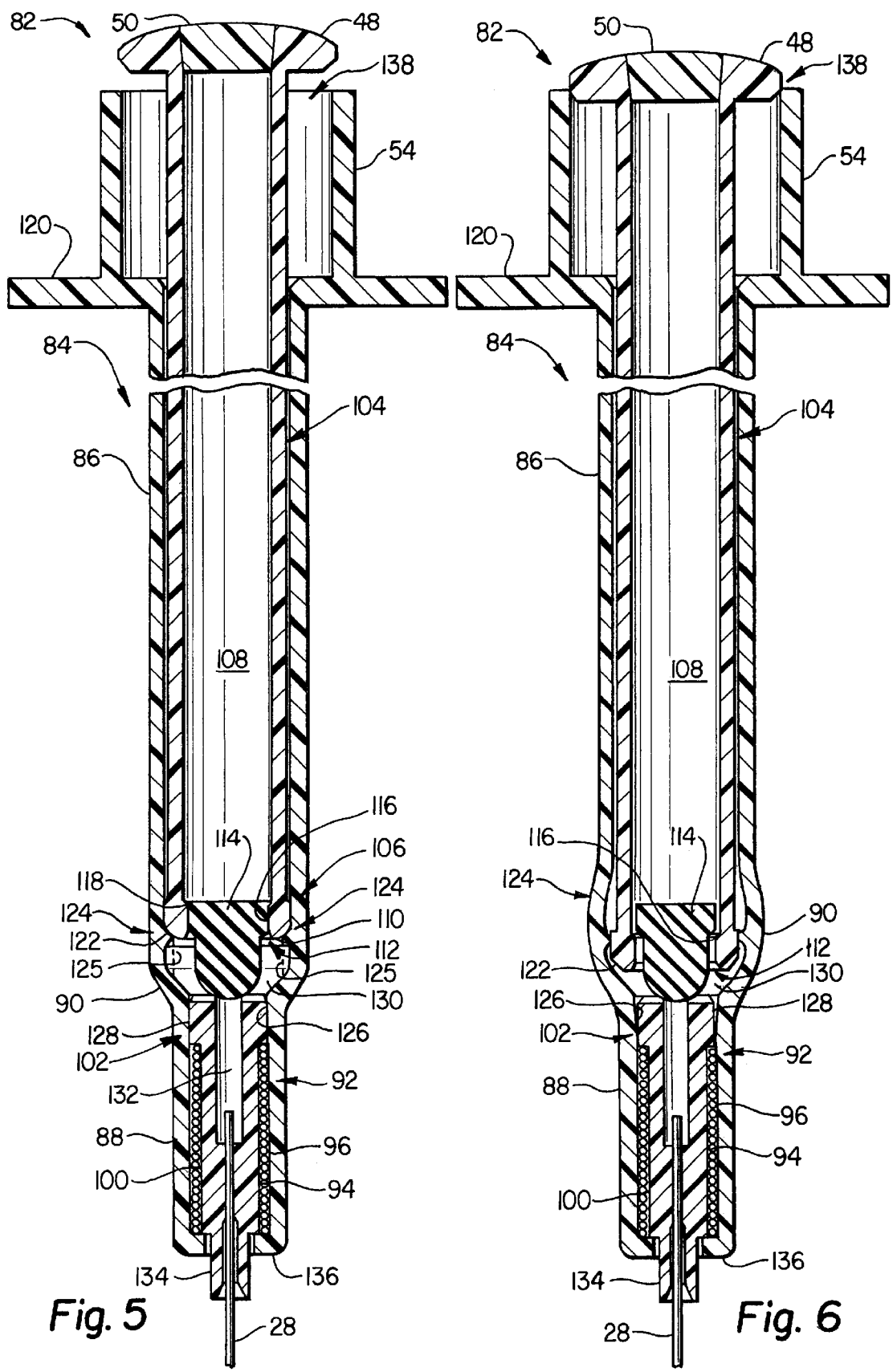

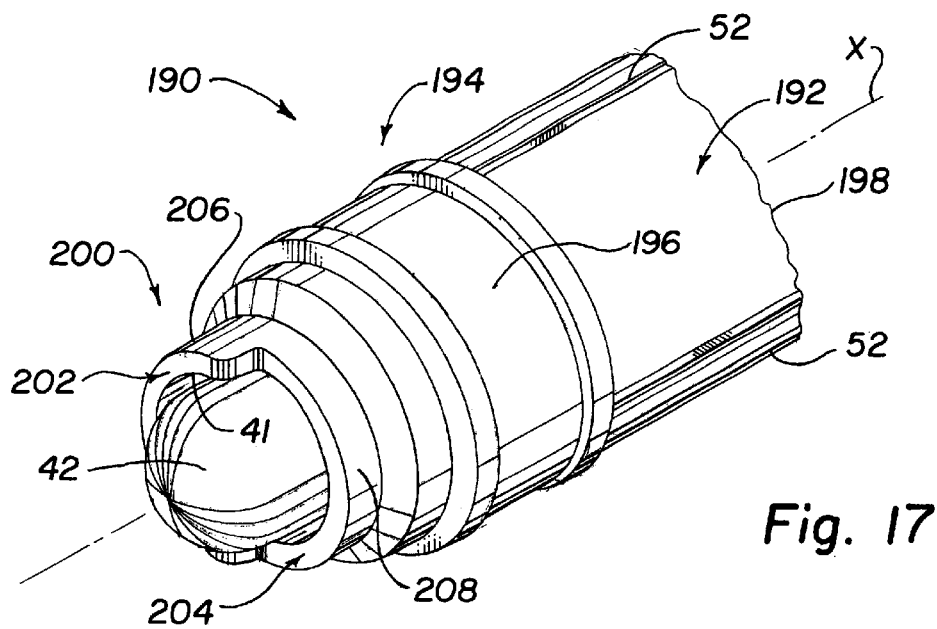
Fig. 17
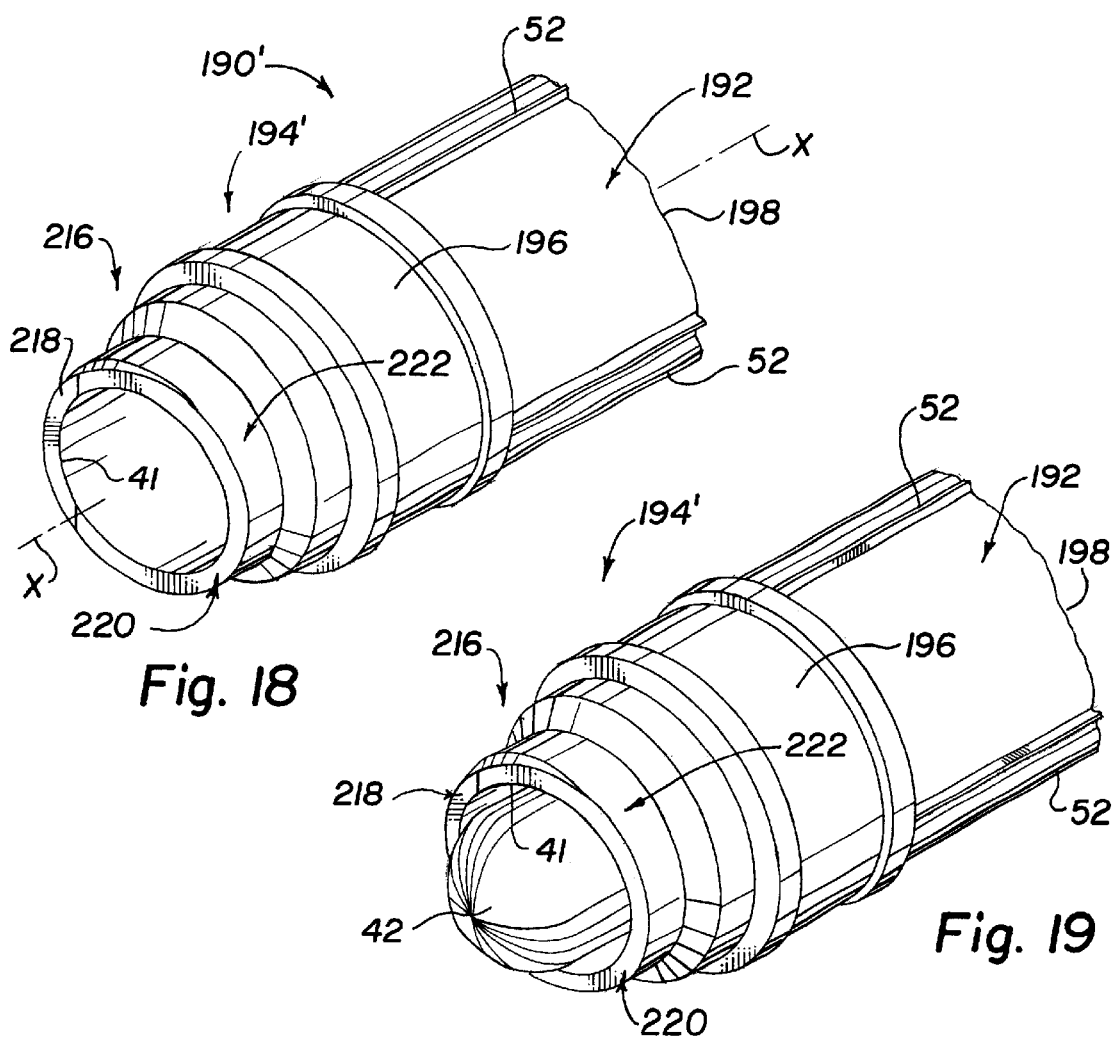
Fig. 18
Fig. 19

RETRACTABLE SYRINGE WITH REDUCED RETRACTION FORCE

FIELD OF THE INVENTION

This invention relates to a medical device, and more particularly to a retractable syringe and components suitable for mass production and assembly having a low triggering force and high blowout pressure which is nonreusable after one use.

BACKGROUND OF THE ART

A major cause to the spread of AIDS in the general population is the presence of IV drug users who share and reuse hypodermic syringes to inject drugs. Infection can be spread from AIDS patients in hospitals and medical facilities through accidental needle sticks from needles used on infected patients. Used syringes with extended needles present a risk to medical personnel and sanitation employees and others in the disposal chain.

The gravity of the threat posed by AIDS and the fact that the main vector of the spread of the dreaded disease is through reuse of syringes by IV drug users has resulted in intense activity to develop the most practical, most reliable, easily assemblable, mass-producible syringe.

There are a number of syringes of different designs which have needles which will retract at the end of the injection cycle. Most of these have never reached the market because of various deficiencies. Prime among the usual deficiencies of the prior art are problems of complexity, reliability, cost and ease of use. The most commonly used syringes are 1 cc and 3 cc syringes which must be mass-produced at the rate of millions per day. Cost is a significant factor both in manufacture of the parts and assembly of the device. High speed production requires molds with 64 cavities or more to reduce unit cycle time. Therefore, molded structures within the barrel that require collapsing core pins such as are shown in much of the art are unlikely to be producible at competitive costs.

One of the problems of the prior art of retractable syringes is the sheer number and complexity of parts which must be formed and assembled. Other problems with the prior art are dependence on flexing or breaking of internal parts by the plunger in order to release the retraction mechanism and use of a diaphragm at the end of the plunger which must be penetrated by a needle holding member and spring. These structures present serious quality control and assembly problems. Small broken off pieces can present a risk of hang-ups. Hooks are often used to releaseably secure retraction mechanisms. Hooks present difficult holding and control problems, may cause retention of air bubbles upon filling and may be undesirably temperature sensitive.

The prior art frequently has a two-piece barrel in order to be able to assemble a retraction device in the nose. This requires at least an additional part and assembly step. It is still necessary to pass the sharp injection needle through a small opening often while compressing a spring before the two parts can be assembled. The tiny needles are produced in the form of coil tubing and vary significantly from straightness after they are cut to length. This leads to difficult assembly problems if the needle must be passed through a small opening. The extremely sharp tip will catch the edge of a hole and jam the production line.

The rare prior art that employs a front mounted retraction mechanism in a one-piece barrel with a plugged hollow plunger, Tsao U.S. Pat. No. 5,084,018, among other things does not show reduced barrel area to prevent excessive blowout pressure, employs engaging flanges to secure all retraction parts, requires concurrent distortion of internal parts and flanges to effect release, cumulating in excessive force required to retract and requires ventilation holes because of a compartmented barrel.

The prior art has not produced a retractable nonreusable tamperproof syringe for mass production and assembly which is simple, reliable, cost effective, easy to use and retract, looks like a conventional syringe, has few parts which are easy to make and assemble, is not temperature sensitive and not subject to danger of premature retraction.

The prior art has not recognized a retraction mechanism with separable parts that relies entirely on clamping force or friction at a smooth walled reduced diameter transition zone in the barrel with mating lands which are slidably or separably released in response to relatively low thumb pressure while having resistance to premature retraction and high blowout pressure resulting from high pressure produced in the fluid chamber during an injection. The prior art has not recognized that such a structure can be molded as a one piece outer body over a core that can be pulled out from behind allowing the retraction mechanism to be easily pushed into place from behind, steered by the narrow nose portion. Neither does the prior art in such a combination realize the desirable non-cumulation of forces resisting retraction in order to minimize the thumb force required, having a most simple tamperproof feature and the fewest number of easily made parts.

The syringe plunger assembly has a combination of features not found in a prior art syringe. A head end which acts like a piston when installed in a syringe barrel has a reduced diameter front end having an opening and a dislodgeable stopper slidingly mounted in the opening projecting forwardly from the tip. Cooperating lands within the opening and on the head of the dislodgeable stopper seal the opening into the hollow interior of the plunger. The area of the stopper is relatively small when compared to the area exposed to the piston, which compresses fluid in a chamber below the piston. The ratio of the total area of the fluid chamber to the fluid exposed area of the stopper is at least two to one, more preferably three to one or more so that the stopper requires less holding force without blowing out back into the internal cavity. The cooperating lands have sufficient length so that the stopper can move back to the tip when the plunger moves forward at the end of an injection stroke without unsealing the plunger opening. A reduced holding force is sufficient to prevent blowout of the stopper after the stopper has been moved back to the tip because the stopper is exposed to a lower pressure generated force because of its relatively smaller area. The back of the plunger is vented so that entry of retractable parts which upon retraction finish dislodging the stopper and carry it back into the cavity, do not generate internal pressure that can blow out the nose of the syringe carrying any residual fluid with it. The thumb cap on the plunger is received and recessed into the opening at the back of the barrel when retraction occurs. The plunger cannot be grasped after this occurs to help prevent reuse.

These features and more are found in the inventive combination herein further disclosed which is especially suited for high speed production and assembly at low cost.

SUMMARY OF THE INVENTION

The invention is a reliable retractable tamperproof syringe having multiple tamperproof features which operates on a principle which permits low cost parts which are few in number and well suited for high speed mass production and assembly. The syringe structure features a one piece hollow outer body having a longitudinally extending wall which is stepped. The wall comprises an elongated barrel and nose with a transition zone connecting the barrel and nose. The nose has a reduced diameter relative to the barrel. The outer body has an inwardly facing surface in the wall at the most constricted part of the transition zone where the nose begins. A plunger assembly is disposed partially within the elongated barrel with an end cap for depression of the plunger extending from an opening in the back of the barrel. The head of the plunger, which has a retraction cavity for receiving parts of a retraction mechanism, moves in slidable sealed contact with the interior of the barrel.

A retraction mechanism is lodged in the nose of the body. The retraction mechanism comprises an elongated needle holder and spring combination wherein the needle holder has an elongated body with a needle holding portion in front and a head in back. The head of the needle holder has a cooperating outwardly facing surface configured to cooperate with said inwardly facing surface along an interface oriented in the direction of retraction to produce a holding force on the needle holder when installed in the nose in the unretracted position. The needle holder and spring are easily installable from the rear of the barrel toward the nose and releaseably held by sliding engagement of said cooperating inwardly and outwardly facing surfaces while compressing the spring and thereby producing a holding force on the needle holder in opposition to the retraction force applied to the needle holder by the spring. The parts are circular in cross section.

The outwardly facing surface on the circular head of the needle holder is slightly greater in diameter than the circular inward facing surface in the wall at the most constricted portion where the nose begins. The needle holder is thus clamped in position by hoop stresses induced in the outer body and held in position by frictional holding force. The needle holder is released in response to depression of the plunger to a retraction position. Retraction occurs in response to thumb force on the plunger when a portion of the plunger passing into the transition zone separates at least a portion of the inwardly and outwardly facing cooperating surfaces thereby reducing the holding force on the needle holder to an amount less than a retraction force on the needle holder produced by the spring whereby the needle holder is retracted into the cavity a distance sufficient to withdraw an injection needle, attached to the needle holder, into the outer body.

In one embodiment, the head of the needle holder is a two part head comprising an inner head surrounded by a separable retainer member wherein the outer surface of the retainer member is the outwardly facing surface with cooperates with the inwardly facing surface in the wall to retain the needle holder in an unretracted position at the most constricted part of the transition zone where the nose begins. The retainer member is a ring member coupled to the inner head along a sliding interface oriented in the direction of retraction with a friction force which exceeds the retraction force provided by the spring. The front of the needle holder is grounded in the nose portion against forward movement. The plunger head is configured to pass through the most constricted area and push against the retainer member without also pushing against the head of the needle holder. An alternate construction of the two part head of the needle holder comprises the separable retainer member being tack welded to the inner head of the needle holder, preferably along a very small ridge or bridge between the mating surfaces which holds the two part head together until the bridge is ruptured by movement of the plunger after an injection has occurred.

The front of the plunger has an opening for a stopper slidingly fitted therein in an interference fit. The stopper is fitted in the opening in an interference fit along a sliding interface oriented in the direction of retraction. The stopper is mostly or fully dislodged by contact with the retraction mechanism at the end of an injection cycle by continued depression of the plunger from a first position at the end of the injection cycle to a second position with the tip of the plunger in contact with the retainer ring. This avoids cumulation of the force on the plunger required to dislodge the stopper from the opening and the force required to dislodge the retainer member from the head of the needle holder and outer body wall. Upon further depression of the plunger from the second position to the retraction position, the frictional holding force on the needle holder is reduced until the retraction force provided by the spring exceeds the remaining holding force and the needle holder and needle connected thereto are ejected into the cavity carrying the dislodged stopper along with them. The dislodging of the stopper and the retainer member alone make the syringe non-reusable. The plunger cannot be removed after retraction because the graspable end cap enters an opening at the back of the barrel when the plunger is depressed to the retraction position to prevent tampering after retraction.

The retraction cavity of the plunger is preferably vented to prevent a puff of air coming forward at the instant of retraction from blowing a tiny amount of retained fluid from the nose. This condition can occur if the plunger is fully depressed to release the needle holder and dislodge the stopper while the needle is physically restrained from retracting by the septum of a vial which has just been filled with fluid from the syringe. The thumb cap at the rear of the syringe is preferably provided with channels in fluid communication with the interior in cooperation with a closure removably installed in a centrally located opening in the thumb cap. One or more stepped portions of the opening and closure provide seating for the closure. Undercut portions at the side of the closure together with grooves in the interior surface of the plunger wall create passages for air to vent through channels on the thumb cap. This structure prevents air from being trapped by the user's thumb when the thumb cap is pressed to fire the syringe. One or more slots at the back of the barrel around the opening which receives the thumb cap prevent vented air from being trapped by the user's thumb when the plunger is fully depressed.

The syringe has a high blowout pressure and a low plunger thumb force required to cause retraction. Blowout pressure is the fluid pressure operating on the stopper and retainer ring during an actual injection. High blowout pressure resistance is obtained because the retainer ring is mounted in the most constricted portion of the barrel where the nose begins which significantly reduces the amount of area exposed to fluid pressure. The smaller retainer ring allows the use of a small needle holder such that the opening in the plunger and the stopper can be only a fraction of the cross sectional area of the fluid chamber below the plunger head. The ratio of the greatest cross sectional area of the variable chamber and that of the dislodgeable stopper or the ring member are selected so that the maximum expected thumb force on the plunger during an injection will produce a maximum pressure in the chamber which will generate a blowout force on the stopper and retainer member slightly less than the amount of dislodging force necessary to dislodge the stopper and retainer member during retraction. This ratio should be at least two to one, or more preferably three to one or more, in order to ensure against premature blowout of the stopper or retainer ring.

In an alternate embodiment, the fewest number of easily made separate parts are used in a retractable syringe. The alternate embodiment has a similar stopper in the head of the plunger and a similar needle holder and spring combination with mating cooperating inwardly facing and outwardly facing interengaged surfaces at the most constricted part of a transition zone where the nose begins. In the alternate embodiment, there is no retainer ring around the head of the needle holder. Instead a tiny ramp is provided at the transition zone or adjacent the transition zone whereby the head of the plunger gently spreads the barrel outwardly while dislodging the stopper thereby reducing the clamping or friction force on the head of the needle holder provided by the wall of the outer body. The holding force is thereby reduced below the retraction force provided by the compressed spring and the needle holder is ejected into the cavity of the plunger carrying the dislodged stopper along with it.

A modification of the front tip of the syringe plunger has surprisingly been found to reduce the amount of plunger force required to initiate and complete retraction of the retraction mechanism shown in FIGS. 1–3. The modified front tip of the plunger is an irregular shape configured such that one portion of the tip is advanced beyond the remainder of the tip. When the plunger is moved forward after the end of an injection to initiate retraction, the advanced portion of the tip contacts one portion of the transversely positioned retainer before it contacts the remainder of the retainer thereby moving the one portion of the retainer relative to the wall surface of the barrel and tilting the retainer as the retainer member is being separated by the plunger from the needle holder of the retractable needle. In one modified form of the improved syringe plunger handle, the front tip end portion has a longitudinally varying front surface comprising a stepped front contact surface having a high step and a lower step with the high step being a forwardly extended portion of the tip. The high step first pushes against the retainer member and moves one portion of it forward when the plunger moves forward at the end of an injection. In an alternate preferred embodiment of the modified syringe plunger handle, the longitudinally varying front surface is generally angled with respect to the longitudinal axis of the syringe such that one part of the front surface of the tip first presses against part of the retainer member when the plunger moves forward at the end of an injection. In a variation of this structure, a portion of the front contact surface at the forwardmost extending part of the tip has a flat transversely oriented surface which is the part which first contacts the transversely positioned retainer and moves one part of the retainer before the remainder of the contact surface contacts the rest of the retainer to move the retainer ring and separate the retainer member from the needle and needle holder.

Manufacture and assembly is facilitated by the fact that the plunger and the outer body can be molded with a non-collapsible core tool that can be pulled out from behind. The parts are simply shaped and do not have hooks and parts with reentrant angles that require collapsible core pin technology. The outer body can be made in one piece and assembled from the rear. The narrowed nose portion provides no lateral space with will permit bunching of the spring and jamming when the retraction assembly is moved forward in the outer body. In fact, the nose serves as a guide to steer the parts into the proper position in one smooth stroke.

The needle does not have to be installed before the retraction mechanism is put in place because it is readily installed from the front after the needle holder is slidingly lodged in the nose. Significant variations in the holding force on the needle holder and the dislodging force on the stopper due to slight variances in the tolerance of the mating parts is avoided because the longitudinal wall of the outer body has some flexibility. The wall can spread outwardly slightly and the stopper and head of the needle holder can compress slightly radially and expand slightly in the longitudinal direction to avoid significant changes in the holding force caused by small changes in the actual diameters. Consistency in the amount of retraction force is thereby provided and economy is assured.

BRIEF DESCRIPTION OF THE DRAWINGS

FIG. 1 is a cross section along the central axis of a first embodiment of the invention with the plunger positioned in a first position at the end of an injection cycle;

FIG. 2 is the syringe of FIG. 1 with the plunger depressed additionally to dislodge the stopper at a second position of the plunger wherein the tip of the plunger is ready to operate the retraction mechanism;

FIG. 3 is the syringe of FIG. 2 wherein the plunger has been further depressed to a retraction position, retraction has occurred and the cap at the back of the plunger is closely received in an opening at the back of the outer body;

FIG. 4A is a partial cross section on the entral axis of an alternate tamperproof opening in the back of the outer body prior to retraction;

FIG. 4B is the structure of FIG. 4A with the plunger in the retracted position received in an opening at the back of the outer body;

FIG. 5 is a cross section along the central axis of a simplified alternate syringe structure without a retainer member around the needle holder, which is released by separation of the friction surfaces, shown in the plunger position which represents the end of an injection cycle;

FIG. 6 is the syringe structure of FIG. 5 wherein the plunger is further depressed to dislodge the stopper and begin to release the friction surfaces just prior to retraction;

FIG. 17 is a cut away perspective view of a reduced force syringe plunger handle for the syringe of FIGS. 1–3 or 9 showing part of the plunger and the modified plunger head having a plunger seal and a stepped front end tip portion with a releasable plug member shown extending from the opening in the tip leading into the retraction cavity;

FIG. 18 is a cut away perspective view of an alternate form of the modified plunger head of FIG. 17 wherein the front tip portion of the plunger is generally cut at an angle with respect to the syringe axis such that one part of the front contact surface of the tip will press first against the retainer member when the plunger moves forward;

FIG. 19 illustrates the reduced force syringe plunger handle head and part of the plunger of FIG. 18 further including the releasable plug member positioned for use in the opening at the front of the syringe leading to the retraction cavity;

DETAILED DESCRIPTION OF THE PREFERRED EMBODIMENT

Figure 7:
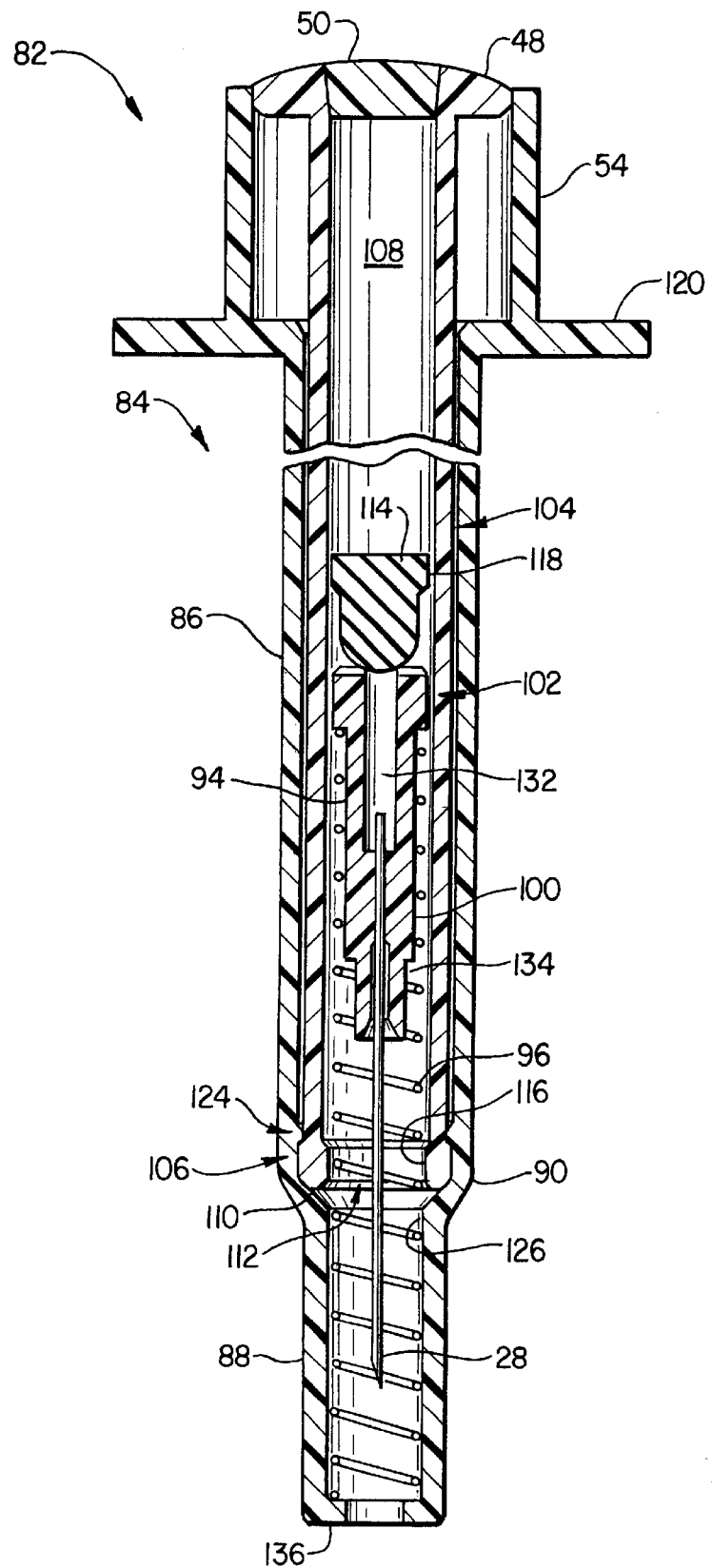
FIG. 7 is the syringe structure of FIG. 6 with the plunger further depressed beyond the position of FIG. 6 to the retraction position where retraction has occurred and the cap is secure within an opening in the back of the hollow outer body.

In the description that follows, like parts will be referred to by the same reference numerals. Parts with a subscript letter are mean to illustrate a minor variation of a part with the same number. The drawings are enlarged significantly in order to show the details of the invention but generally reflect the true scale which is contemplated. The parts as shown are understood to be preferably circular and symmetrical as is conventional for syringes. The drawings reflect a syringe structure typically having a 1 cc to 3 cc injection fluid capacity.

FIG. 1 shows the structure of the first embodiment generally referred to by reference numeral 10. Syringe 10 has a one piece hollow outer body 12. Body 12 has a longitudinally extending wall comprising an elongated barrel 14 and a nose 16 with a transition zone 18 connecting the barrel and nose. A front mounted retraction mechanism lodged in the nose is generally referred to by the reference numeral 20. It comprises the combination of an elongated needle holder 22 and spring 24. The needle holder has an elongated body with a needle holding portion 26 in front for holding a needle 28 and a head 30 in back. Head 30 may consist of a two part head as in FIGS. 1–3 or a one part head as in FIGS. 5–7. The needle holder is released by depression of a plunger that will be described.

A plunger generally designated by the reference numeral 32 is disposed for use partially within barrel 14. The plunger has a head and seal generally referred to by reference numeral 34, in slidable sealed contact with the interior of barrel 14 of outer body 12. The plunger has a seal element 36 that is conventional and a retraction cavity 38 therein.

Head 34 has a tip portion 40 forming an opening 41 into retraction cavity 38. A resilient dislodgable stopper 42 is sealingly positioned in opening 41 with a front portion thereof extending beyond tip 40. Head portion 34 and the back part of stopper 42 have cooperating lands 44, 46, respectively, which seal opening 41. Plunger 32 has an end cap 48 for depression of the plunger by the thumb. End cap 48 has a central opening for permanently receiving force fit plug 50 to close retraction cavity 38 at the back end.

A plurality of longitudinally extending flutes 52 slidingly support plunger 32 in barrel 14. In the embodiment of FIG. 1, outer body 12 has a collar 54 extending behind finger grips 56 having opening 58 which closely receives the outer periphery 60 of cap 48 when the plunger is depressed to the retracted position. An alternate arrangement is shown in FIGS. 4A and 4B in which barrel 14 is extended longitudinally, if necessary, so that end cap 48 fits closely within an opening at the back of the barrel where the finger grips are. FIG. 4B shows the tamperproof position with the plunger in the retracted position. It should be noted that depending on the relationship of the inside diameter of the barrel and the diameter of the end cap, the end cap could instead be received right inside the opening at the back of the barrel. Regardless of how the end cap in back of the outer body and barrel are configured, the plunger can no longer be grasped after retraction has occurred because end cap 48 is depressed into an opening.

The wall of outer body 12 and head 30 of the needle holder have mating cooperating smooth surfaces which hold needle holder 22 in the position shown in FIG. 1 with spring 24 compressed. Nose 16 has a reduced diameter relative to the barrel. The outer body has a most constricted part where head 30 of needle holder 22 is engaged and held. The outer body has an inwardly facing surface 62 at the most constricted part of the transition zone where nose 16 begins. Similarly, head 30 has an outwardly facing surface 64 configured to cooperate with inwardly facing surface 62 to produce a holding force on needle holder 22 when the retraction mechanism is installed in the nose from the rear. Mating surfaces 62, 64 constitute a sliding interface oriented in the direction of retraction, which seals nose 16. Mating surfaces 62, 64 are preferably friction surfaces which have an interference sliding fit to apply a frictional holding force which holds needle holder 22 in position by friction between the mating parts. It is within contemplation of the invention that one or more of the cooperating interface surfaces could employ a coating or adhesive bond which is ruptured or released when the mating surfaces or lands are separated or moved relative to each other.

Head 30 provides a lower boundary for a variable fluid chamber 68 below head 34. Needle holder 22 has a fluid path 70 in fluid communication with fluid chamber 68 and needle 28. Needle holder 22 has a smaller diameter inner head 72 which is part of head 30. Retainer member 66 is coupled to inner head 72 along sliding interface 74 oriented in the direction of retraction. Retainer member 66 is coupled to inner head 72 with a holding force which exceeds a retraction force applied to the underside of inner head 72 by means of the end of compressed spring 24. A reduced diameter portion 27 of needle holder 22 protrudes through an opening in front 76 of nose 16.

Importantly, retainer member 66 can be visualized as an annular ring surrounding circular inner head 72. The location of retainer member 66 at the most constricted part of the transition zone where the nose begins and the relatively small area exposed to pressurized fluid in chamber 68 results in a high blowout pressure. Since the front portion 26 of the needle holder is grounded or bottomed inside front 76 of nose 16, no amount of pressure will allow needle holder 22 or needle 28 to move forward. Blowout pressure may be defined as the pressure in chamber 68 acting on the exposed area of retainer member 66 to produce a force sufficient to overcome the holding force such that retainer 66 could "blowout" by moving forward and prematurely release needle holder 22.

Some users have strong hands and might, at the outer limit in an emergency, be able to generate a force of as much as fifteen to eighteen pounds on the plunger during an injection. It is considered almost impossible, for anyone to exert a force of more than eighteen pounds. This may be regarded as the maximum expected force which must be taken into account so that ring member 66 will not blowout while an injection is being made. The greatest cross sectional area of variable chamber 68 and the area of retainer member 66 exposed to fluid pressure are selected so that the blowout pressure is higher than the maximum pressure in chamber 68 expected to result from the maximum expected thumb force applied to cap 48 during an injection. This ratio is preferably about two to one and more preferably about three to one or more so that the holding force holding the retraction mechanism in place can be kept at a comfortably low level while the blowout pressure remains high.

Dislodgeable stopper 42 has a similar blowout problem to recognize. The front and middle portion of stopper 42 are relieved slightly from opening 41 such that the fluid pressure in chamber 68 is directed against the cross sectional area at cooperating lands 44, 46 and could cause stopper 42 to blowout. A frictional holding force is generated at the lands 44, 46 which may be called a dislodging force which must be overcome to slide stopper 42 rearwardly before retraction. The ratio of the maximum cross sectional area across the interior of variable chamber 68 to the maximum cross sectional area of stopper 42 exposed to pressure in chamber 68 are selected so that the maximum expected thumb force on plunger 32 during an injection will produce a maximum force slightly less than the amount of dislodging force necessary to dislodge the stopper so that stopper 42 will not blowout during an injection. This ratio is preferably not less than about two to one, more preferably three to one or more, whereby a force of about eighteen pounds on the plunger, for example, would produce a pressure generated force of only about nine or six pounds, respectively, on the stopper, so that the stopper can be easily dislodged in advance of retraction at the end of the injection cycle but will not blowout during an injection. The stopper is dislodged after the injection by thumb force applied to the stopper by movement of the plunger.

The components used for retraction are arranged to avoid cumulation of force during the retraction sequence. In FIG. 1, stopper 42 has a forward extension beyond tip 40 which allows full thumb pressure to be applied to the stopper before any other portion of the retraction mechanism is engaged. The amount of forward extension beyond tip 40 is related to the length of lands 44, 46 such that the forward extension of stopper 42 preferably represents about 80 percent of the engaged land length. When stopper 42 is moved back until the front is even with tip 40, as seen in FIG. 2, only about 20 percent of engaged land remains. In FIG. 2 it can be seen that thumb force on plunger cap 48 has been applied to partially dislodge stopper 42 such that a gap 78 is created and the remaining engaged land area is represented as area 80.

Since I believe the amount of frictional holding force or dislodging force is roughly proportional to the amount of the length of the sliding interface between cooperating lands 44, 46, it follows, ignoring dynamic effects, that the amount of force remaining decreases as the engaged sliding interface area is reduced. This is what happens as stopper 42 moves back into cavity 38 from the position of FIG. 1 to the position of FIG. 2. It is believed appropriate to set the initial dislodging force to allow about five pounds at the position of FIG. 1 which is reduced to about one pound remaining when the stopper or plug member 42 reaches the position of FIG. 2. It might be noted at this point in the description that the front portion of tip 40 preferably has some longitudinally extending slits or openings so that fluid is not trapped in the trapezoidal shaped area of chamber 68, seen in FIG. 2, because of contact between tip 40 and the upper surface of retainer ring 66.

Needle holder 22 and spring 24 are combinably installable from the rear of the barrel before the plunger is assembled and releasably held at the most constricted part of the transition zone where the nose begins by sliding engagement of the cooperating inwardly and outwardly facing friction surfaces 62, 64 while compressing spring 24. The length of the engaging land 64 and the amount of interference fit is preferably designed to provide a frictional holding force in opposition to the retraction force provided by the compressed spring 24 of somewhere around five pounds even though the spring may apply a retraction force in the retraction direction of somewhere around a half pound. In use the needle is pushed against a rubber seal in a vial so the needle holder must resist a resulting backward force without being dislodged during the filling operation. This requirement and blowout pressure limits the low end of the holding force on the needle holder.

Referring again to FIG. 2, it can be seen that further depression of the plunger beyond the second position of FIG. 2 dislodges retainer ring member 66 along the sliding interface 74 provided by the outer surface of inner head 72 and along the inwardly facing friction surface 62. As the amount of remaining engaged interface is reduced, the amount of force required to continue moving retainer member 66 off needle holder 22 is reduced and the small remaining engagement area 80 between lands 44, 46 of the plunger and stopper preferably cause stopper 42 to be dislodged before needle holder 22 is released. When the remaining residual friction force during continued depression of the plunger becomes less than the retraction force provided by compressed spring 24, the retraction position of FIG. 3 is reached whereby retraction occurs.

When retraction occurs needle holder 22 moves through opening 41 into cavity 38. The uncompressed length of spring 24 is selected to provide backward movement sufficient to withdraw an injection needle 28 fixed in front portion 26 entirely within outer body 12, carrying dislodged stopper 42 with it. At the same time, cap 48 enters opening 58 of the barrel with peripheral edge 60 closely confined, in order to prevent tampering after retraction. It is immaterial whether cap 48 moves into the opening at the instant of retraction or after retraction has already occurred because the movement is automatic due to the continued thumb force applied to trigger the retraction. Sufficient unengaged length of inwardly facing friction surface 62 is provided so that retainer member 66 can move downwardly a sufficient distance to reach the retraction position of FIG. 3. After retraction, retainer member 66 preferably remains stuck and prevents any possibility of any one being able to reengage it with the head of needle holder 22. The diameter of land 62 in the area designated 63 can be increased slightly to provide relief for retainer ring 66 as it is pushed down by tip 40.

Figure 8:
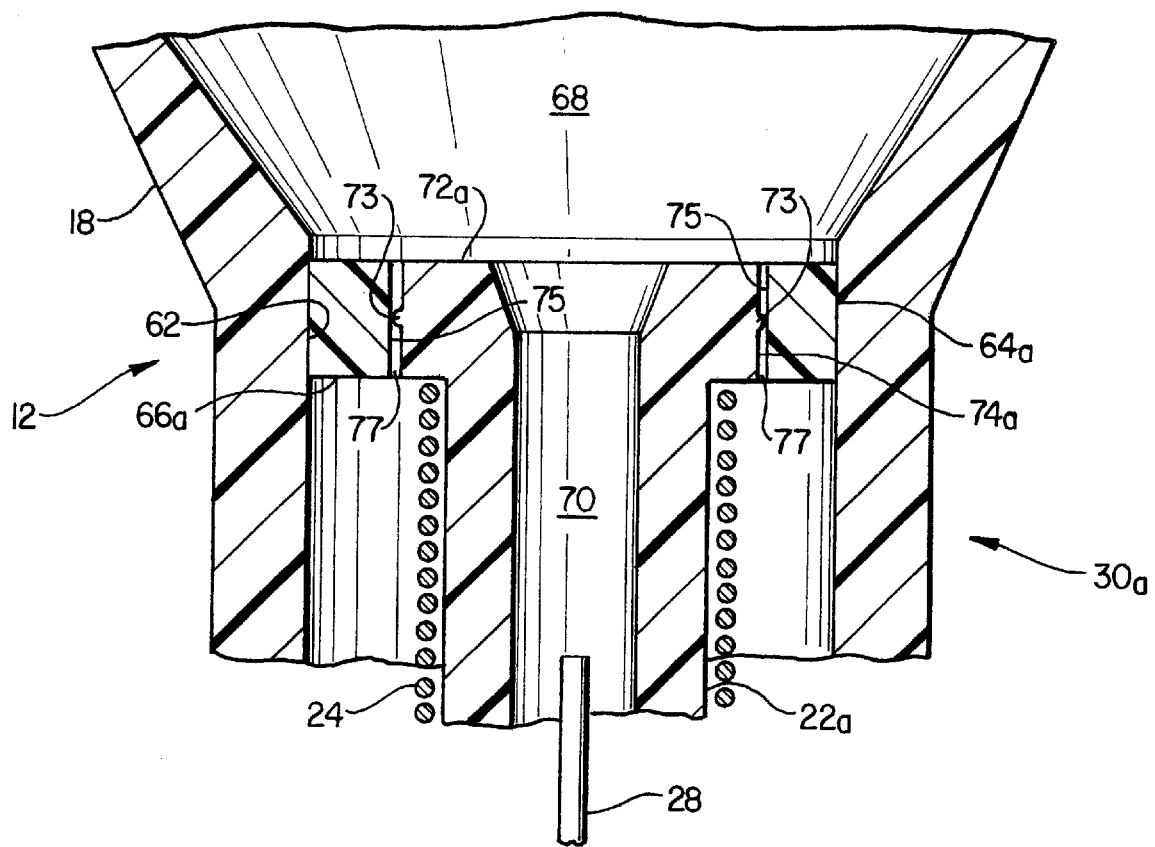
FIG. 8 is a schematic longitudinal cutaway view in elevation through the center of the two part head showing how a tack weld can be applied to simultaneously seal and hold the retainer ring in place on the needle holder.

It is also within the contemplation of the invention that separable retainer member 66 may be removably coupled to inner head 72 of needle holder 22 by means of a relatively small in area "tack" weld which is sufficient to resist the retraction force applied to needle holder by spring 24 but which can be ruptured or separated by depression of the plunger beyond the position shown in FIG. 2, to release the needle holder and allow retraction. This is schematically illustrated in FIG. 8 with respect to alternate head 30a with the parts of syringe body 12 and needle holder 22. cutaway to focus on the modification. The remainder of the syringe structure would be like FIGS. 1–3.

In FIG. 8, inner head 72a has an outwardly facing surface 74a and a very small raised portion or series of horizontally spaced apart raised portions 73 around the periphery in a continuous band or annular ring which extend relatively uniformly outwardly beyond peripheral surface 74a of head 72a. The raised portion could be on the inner surface 75 of retainer 66a instead of being on surface 74a of the needle holder. The head of the needle holder is preferably circular but could be conceivably another shape with the retainer member 66a correspondingly configured to conform to it.

The inwardly facing surface 75 of inner head 72a is in contact with raised portion 73 on the outer surface of inner head 72a and there may be a small gap 77 between them all around. The raised portion 73 couples retainer 66a to inner head 72a and may be referred to as a bridging portion which resists the blowout pressure referred to above and holds the needle holder in place against the retraction force imposed on the needle holder by spring 24 together with any small additional forces that may be applied when the needle is pushed against the rubber seal of a vial in preparation for use. The bridging portion may be formed by "tack" welding the raised portion 73 to the inner surface of the ring 66a or by providing any other form of frangible bridging portion that holds the separable ring member 66 and needle holder head 72a together. It is required that however done, the bridging portion must also serve as a seal between the facing surfaces of the ring member and inner head so that fluid under pressure cannot pass from chamber 68 through gap 77 to reach the nose portion of the device. All fluid must pass through fluid passage 70.

It can be seen that when the position of FIG. 2 is reached the front tip 40 of the plunger presses against retainer ring 66a after stopper 42 is almost dislodged and uncouples the retainer ring 66a from the inner head 72a of needle holder 22a. Any tack weld connecting the separable parts at the bridging portion is ruptured, fractured or otherwise separated so as to separate retainer ring 66 a from inner head 72a thus releasing needle holder 22a from further restraint. They and the force applied by spring 24 causes retraction to occur much as before described and shown in FIG. 3.

It is believed that the increased diameter of the raised portion 73 should be within the range of about 1 to 8 thousandths of an inch which may be dictated by the ability of the molding equipment available to produce a consistent bridging portion without defects. It is believed that it may be desirable to employ different polymeric materials for the retainer ring and needle holder to facilitate tack welding, such as a suitable polyvinyl chloride (PVC) for the retainer ring and a suitable polycarbonate plastic material for the needle holder. One way to couple these two parts may be to assemble them and expose them to a temperature of about 120° C. for twenty minutes or so to allow some diffusion or incipient melting to occur where they touch. The raised portion creates a high unit pressure where it comes into contact with the inwardly facing surface of retainer 66a. Sonic welding could also be employed. A coating or adhesive which couples the retainer ring to the needle holder and can be uncoupled by means of force applied to the retainer ring by the plunger is also within the contemplation of the invention.

An alternate syringe 82 is disclosed in FIGS. 5–7. In FIG. 5, Syringe 82 has a one piece hollow outer syringe body 84. Body 84 has a longitudinally extending wall comprising an elongated barrel 86 and a nose 88 with a transition zone 90 connecting the barrel and nose. A front mounted retraction mechanism lodged in nose 88 is generally referred to by the reference numeral 92. It comprises the combination of an elongated needle holder 94 and spring 96. The needle holder has an elongated stem body with a needle holding portion 100 in front for holding needle 28 and a head 102 in back. In this case, head 102 is a one part head integral with the rest of needle holder 94. Spring 96 delivers a retraction force in a retraction direction to the underside of head 102.

A plunger generally designated by reference numeral 104 is disposed for use partially within barrel 86. Plunger 104 has a head portion 106 which moves in slidable sealed contact with the interior of barrel 86 of outer body 84. Although a separate seal might be used on head 106, this embodiment is suitable for a smaller diameter, such as a 1 cc syringe, and can be used with head 106 also serving as the seal. A retraction cavity 108 is provided in the interior of hollow plunger 104. Head 106 has a tip portion 110 forming an opening 112 for a dislodgable stopper 114 having a front portion extending beyond tip 110. Head portion 106 has an inwardly facing land 116 and the back of stopper 114 has an outwardly facing land 118 comprising cooperating friction surfaces which seal opening 112. The back portion of outer body 84 may have finger grips 120 and the same collar 54 and end cap 48 previously disclosed. The alternate arrangement of FIGS. 4A and 4B may also be employed.

The outer portion of tip 110 may be equipped with an angled surface 122 designed to cooperate with a small ramp surface 124 located in the vicinity of transition zone 90. The wall of outer body 84 and head 102 of the needle holder have mating cooperating friction surfaces which frictionally hold needle holder 102 in the position shown in FIG. 5 with spring 96 compressed. Nose 88 has a reduced diameter relative to barrel 86. The outer body has a most constricted part where the head 102 of needle holder 94 is frictionally engaged. The outer body has an inwardly facing surface or land 126 at the most constricted part of the transition zone where nose 88 begins. Similarly, head 102 has an outwardly facing friction surface 128 configured to cooperate with inwardly facing surface 126 to produce a frictional holding force on needle holder 94 when the retraction mechanism is installed in the nose from the rear.

Mating surfaces 126, 128 constitute a sliding interface oriented in the direction of retraction, which seal nose 88. Mating surfaces 126, 128 are preferably smooth friction surfaces which have an interference sliding fit when needle holder 94 is installed from the rear whereby a frictional holding force holds needle holder 94 in position by friction between land 126 and head 102 of needle holder 94. It is within contemplation of the invention that one or both of these surfaces could have a coating or adhesive bond which is ruptured when the mating surfaces are separated to release the needle holder.

Head 106 provides the upper boundary for a variable fluid chamber 130 below head 106. Needle holder 94 has a fluid path 132 in fluid communication with chamber 130 and needle 28. Needle holder 94 is releasably coupled at surfaces or lands 126, 128 with a holding force that exceed the retraction force applied to the underside of head 102 by the end of compressed spring 96. A reduced diameter portion 134 of needle holder 94 protrudes through an opening in front 136 of nose 88. Blowout pressure is not a factor with respect to the needle holder on the alternate embodiment. No amount of pressure will allow needle holder 94 or needle 28 to move forward since the front portion 100 of the needle holder is grounded or bottomed inside front 136 of nose 88.

Blowout pressure is still a factor to be considered in connection with stopper 114. Blowout pressure would be the pressure in chamber 130 produced by thumb force on cap 48 acting on the cross sectional area of stopper 114 which could overcome the holding force, causing stopper 114 to dislodge from opening 112 prematurely. The ratio of the maximum cross sectional area across the interior of variable chamber 130 to the maximum cross sectional area of stopper 142 exposed to pressure in chamber 130, and the dislodging force necessary to dislodge stopper 144, are selected so that the maximum expected thumb force on plunger 104 during an injection will not cause the stopper to blowout. Yet the stopper will still be dislodged by the dislodging force on the plunger once the front of stopper 114 contacts the retraction mechanism after the injection has ended. The ratio referred to is preferably not less than about two to one, or more preferably about three to one or more, whereby a force of about eighteen pounds on the plunger, for example, would produce a pressure generated force of only about nine or six pounds respectively, on the stopper, so that the stopper can be easily dislodged in advance of retraction at the end of the injection cycle but will not blowout during an injection. The smaller diameter stopper allows two or three times the thumb force to be used during the injection cycle than required to actually dislodge the stopper by direct application of force.

By reference to FIGS. 5–7, the operation and further features of the alternate embodiment are discussed. The syringe is used in the normal manner until the plunger is depressed to the first position of FIG. 5 which is the end of the injection cycle. Stopper 114 has a forwardly extending end which has come into contact with head 102 of needle holder 94 to block fluid path 132. Further depression of plunger 104 toward the position of FIG. 6 mostly or fully dislodges stopper 114 and begins spreading barrel 84 at the transition zone by sliding contact between head portion 106 and ramp 124. Ramp 124 is a very small inwardly extending annular thickening of the wan of barrel 86 which can take many shapes or forms. For example, ramp 124 may be a small step 125 in the wall which continues vertically downward as indicated by the dotted line, which is somewhat exaggerated in FIG. 5.

The barrel is flexible and is spread outwardly a slight amount to the position of FIG. 6 just prior to retraction. Here the mating surfaces 126, 128 are separated an amount which reduces the clamping force on the needle holder 94. The spreading shown in FIG. 6 is greatly exaggerated for illustration. It is estimated that an expansion of only about four thousandths of an inch is sufficient to release needle holder 94 from nose 88. By slight further depression of the plunger from the position of FIG. 6 to the retracted position of FIG. 7, retraction occurs when the retraction force applied by spring 96 exceeds the remaining holding force on needle holder 94. Needle holder 94 then moves through opening 112 into cavity 108 along with a portion of spring 96. The uncompressed length of spring 96 is designed to provide sufficient backward movement to withdraw an injection needle 28 fixed in front portion 94 and carry dislodged stopper 114 with it. At the same time, cap 42 enters opening 138 at the rear of a barrel extension 54 where the peripheral edge is closely confined in order to prevent tampering after retraction.

The location and configuration of ramp 124 is arranged to avoid cumulation of force required during the retraction sequence. Most of stopper 114 should be dislodged by thumb pressure on plunger 104 before significant resistance develops as angled surfaces 122 begin pushing outwardly on ramp 124. The selection of the location of ramp 24 and the angle of the engaging surfaces make it possible to have a fairly smooth continuous force since the dislodging force continuously decreases as the sliding interface area 116, 118 between the plunger and the stopper is linearly decreased. Because ramp 124 is relatively very small, it is still possible to remove a stepped molding core from the rear of the outer body 84. Alternately, ramp 124 can be the smaller diameter step 125 which avoids reentrant angles whereby resistance to removal of the molding core could occur. After retraction, the back of the plunger is unaccessible and there is no way to reach to stopper or the needle holder in order to reinstall them for re-use.

When used normally, syringe 10 may have a small amount of fluid remaining in the variable chamber in the second position shown in FIG. 2 which is, of course, greatly exaggerated in scale. This may amount to no more than a drop or a few drops of fluid in the remaining space above the retraction mechanism. When syringe 10 is fired by pushing down on end cap 48, to the position of FIG. 3, the expanding spring and rearwardly moving needle holder carry any remaining fluid up into retraction cavity 38. Surface tension effects hold the tiny droplets in place along the walls of the plunger and no fluid escapes from nose 16. The syringe is normally used to withdraw fluid from a vial. The fluid is injected into a patient followed by immediate retraction of the needle holder and needle in one step. No leakage of fluid from the nose is observed when the syringe is used to inject fluid into a patient.

It has been discovered, however, that if the needle is forcibly prevented from retracting after syringe 10 is "fired" by pushing down until plunger 48 enters opening 58, the small amount of retained fluid from variable chamber 68 can flow into the nose in the space between the needle holder and nose. If the seal around the head of the needle holder is removed while the needle holder is being restrained from retracting, remaining fluid has time to move down into the nose, but it does not leak out from the opening in the front of the nose. Then if the needle holder is suddenly released and allowed to retract normally, it has been found that leakage of fluid from the opening in the front of the nose could be observed. This undesirable scenario was found to occur under the following circumstances. If the syringe is used to draw blood from the patient, the blood filled syringe is removed from the patient and the needle passed through a rubber septum in a sterile vial. The plunger is then depressed to discharge the patient's blood into the vial. Users expect to depress the plunger fully after the fluid is discharged to retract the needle. When the plunger is depressed fully to cause retraction, the needle cannot retract normally due to the fact it is frictionally held by the rubber septum of the vial. When the empty syringe is then withdrawn from the vial by pulling the needle out of the septum, it immediately retracts. Droplets of fluid were observed on the vial as soon as retraction took place.

Surprisingly, it was found that a small "puff" of air is the source of this problem. If the needle or needle holder is temporarily restrained and prevented from retracting in the normal manner, a brief puff of forwardly directed air is generated when the needle holder is finally allowed to retract. This puff of air was found to emerge from the front of the syringe causing retained fluid trapped around the needle holder to be blown out of the opening left in the nose when the needle holder retracts. It was discovered that if the hollow interior of the plunger is vented, preferably in the area of thumb cap, this condition does not occur and the fluid is entirely retained within the syringe body.

FIGS. 9 through 16 illustrate the syringe generally designated as syringe 10 with a modification on the end cap or thumb cap on the plunger to provide for venting of the hollow interior of the plunger which is the retraction cavity. Insofar as possible the original numbering of FIGS. 1–4 is retained with primes used to indicate differences.

Head 34' of plunger 32' is preferably slightly modified from plunger head 34 of FIG. 2 in the following respects. The elongated plunger has a longitudinally extending generally tubular wall 140 defining a hollow interior along the length of the plunger. The plunger has a head end 34' in front and a rear end portion 142 with a thumb cap 48' behind. The outer side of wall 140 at head end 34' is sealingly surrounded with a resilient plunger seal member 36' which is like a band with a pair of separated raised rings 144. Plunger seal 36' fits in a depression in the outer surface of wall 140 where it is securely held in position and prevented from longitudinal movement. Seal member 36' is adapted to slide in sealed contact with a tubular wall when the plunger is moved within syringe barrel 14. It is within contemplation of the invention to have a raised piston molded as part of the plastic plunger to serve as a plunger seal in place of a separate rubber plunger seal 36', although the rubber seal member is preferred.

Wall 140 at head end 34' of the plunger 32' has a reduced diameter front portion extending forward from seal member 36' terminating at tip 40 at the front of plunger 32'. Tip 40 defines the opening 41 which leads into the hollow interior 38. The internal structure is as shown in FIG. 1. The wall 140 behind tip 40 has a stepped inner side surface comprising a land having an inwardly facing surface and a larger diameter portion extending behind the land into the hollow interior. A separate dislodgeable stopper 42 is slidingly held within the reduced diameter front portion of plunger head 34' by a holding force in excess of the fluid injection pressure force to be expected during use of the plunger in syringe barrel 14. Stopper 42 has a back end portion comprising a land 46 and a reduced diameter front end portion extending forwardly beyond tip 40 a fixed distance to its front 146. The fixed distance is the distance between front 146 and tip 40.

As is seen in FIG. 1, the outwardly facing surface 46 of dislodgeable stopper 42 is in sliding sealed engagement with the inwardly facing surface of land 44 in the plunger wall. These lands cooperate to apply a holding force to the stopper and seal hollow interior 38 of plunger 32' from the expected amount of fluid injection pressure force generated in the variable chamber 68 during an injection. The ratio of the effective area of variable chamber 68 to the area of stopper 42 exposed to fluid pressure is at least two to one and preferably three to one or more as previously indicated. This makes it possible to utilize lower holding forces without blowing out the stopper during an injection. The cooperating lands on the inside of the plunger head and the stopper have sufficient longitudinal length to allow dislodgeable stopper 42 to move the fixed distance between its initial extension at 146 and tip 40 in sliding response to forward movement of the plunger after front 146 of stopper 42 contacts a stop.

As indicated in FIGS. 1–3, front 146 of the stopper 42 encounters head 72 of needle holder 22 which serves as a stop. The fluid opening in head 72 of needle holder 22 is preferably provided with some fine slots or grooves so that fluid can continually enter fluid path 70 as the plunger moves from the position of FIG. 1 to that of FIG. 2. As the position of FIG. 2 is reached, the holding force on stopper 42 is reduced by substantial disengagement of the cooperating lands 44, 46 in preparation for dislodgement of the stopper, without unsealing the hollow interior/retraction chamber 38 within plunger 32'. A notch 148 is preferably provided in the tip to prevent trapping fluid at the tip.

Thumb cap 48' at the rear end portion 142 of plunger 32' includes one or more channels 150 which receive vented air from hollow interior 38. Thumb cap 48' has an opening 152 for a closure 154 best seen in FIGS. 10 and 11. Channels 150 are open at the top for ease of molding although closed channels could also be used.

Figure 10:
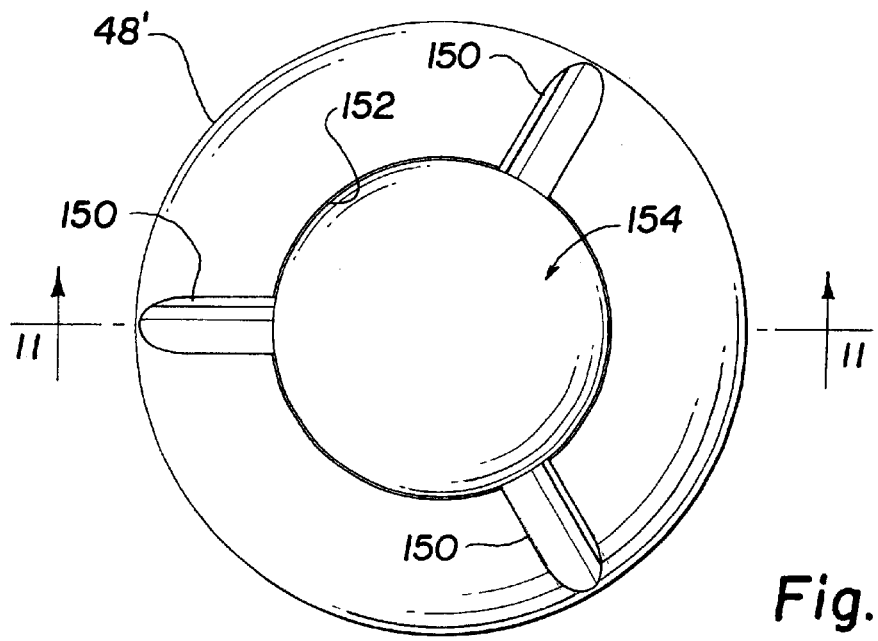
FIG. 10 is a plan view of the thumb cap of the plunger assembly shown in FIG. 9 with the preferred closure.
Figure 11:
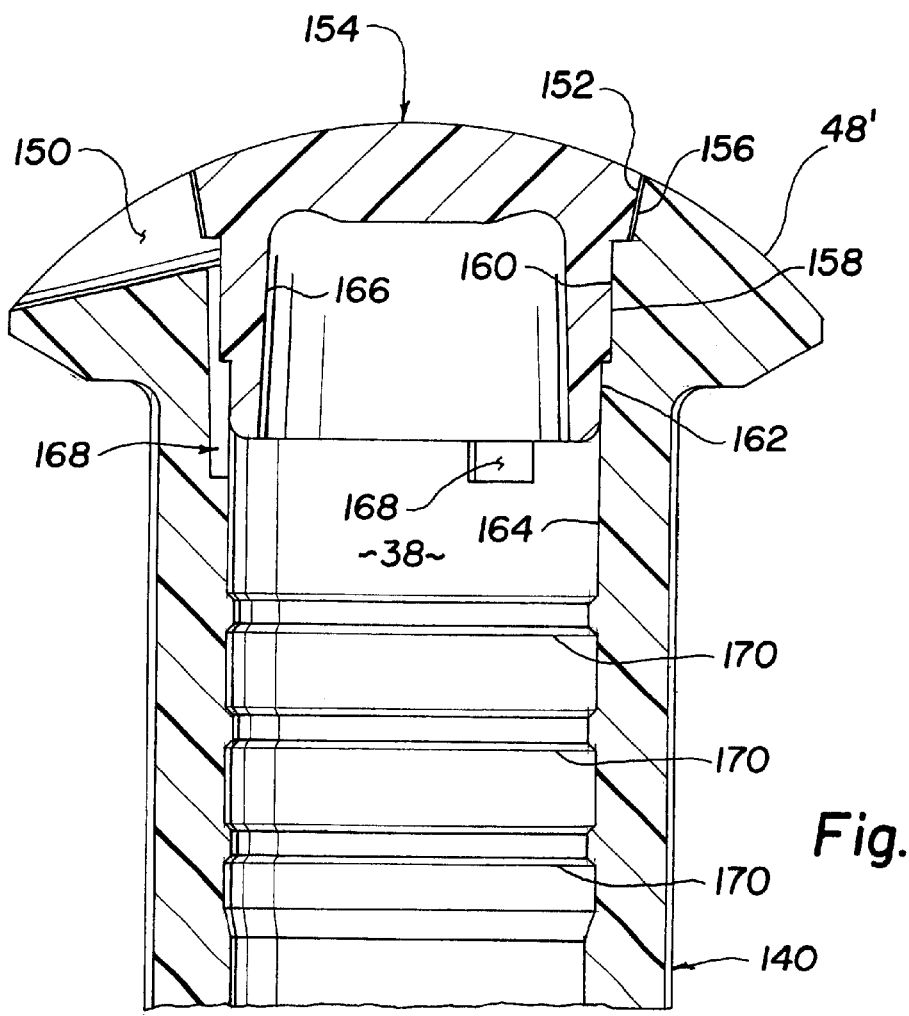
FIG. 11 is a cut away elevational view of the structure at the back end of the plunger and end cap of FIGS. 9 and 10 along line 11—11 showing the preferred closure.

FIG. 10 shows an enlarged top plan view illustrating the use of three channels 150 in combination with a preferred closure 154 installed in circular opening 152. FIG. 11 best shows how the channels 150 receive vented air from hollow interior 38. Closure 154 preferably has a stepped outer surface comprising a rear step 156 which rests in opening 152, an intermediate step 158 which rests in an enlarged portion 160 of the inner side of wall 140 and a front step 162 which rests against inner surface 164 of wall 140. In effect, these structures provide convenient seating for closure 154. Steps 158 and 162 are conveniently provided in a downwardly depending skirt 166.

Importantly, inner surface 164 everywhere there is a channel 150, is provided with a longitudinally extending groove 168 in fluid communication with the hollow interior 38 and the channels 150. Any convenient number may be chosen as the channels are easily molded into the end cap when it is formed. The longitudinally extending grooves 168 do not extend through the entirety of the wall 140 although they could. They are designed for ease of molding since they can formed in the mold that makes the plunger without using separate pins to form an opening. This is an important cost consideration in a multiple out high speed molding process. This structure is designed for preventing the user's thumb from obstructing the vent opening leading from the interior of the plunger thereby assuring that venting will take place.

Figure 9:
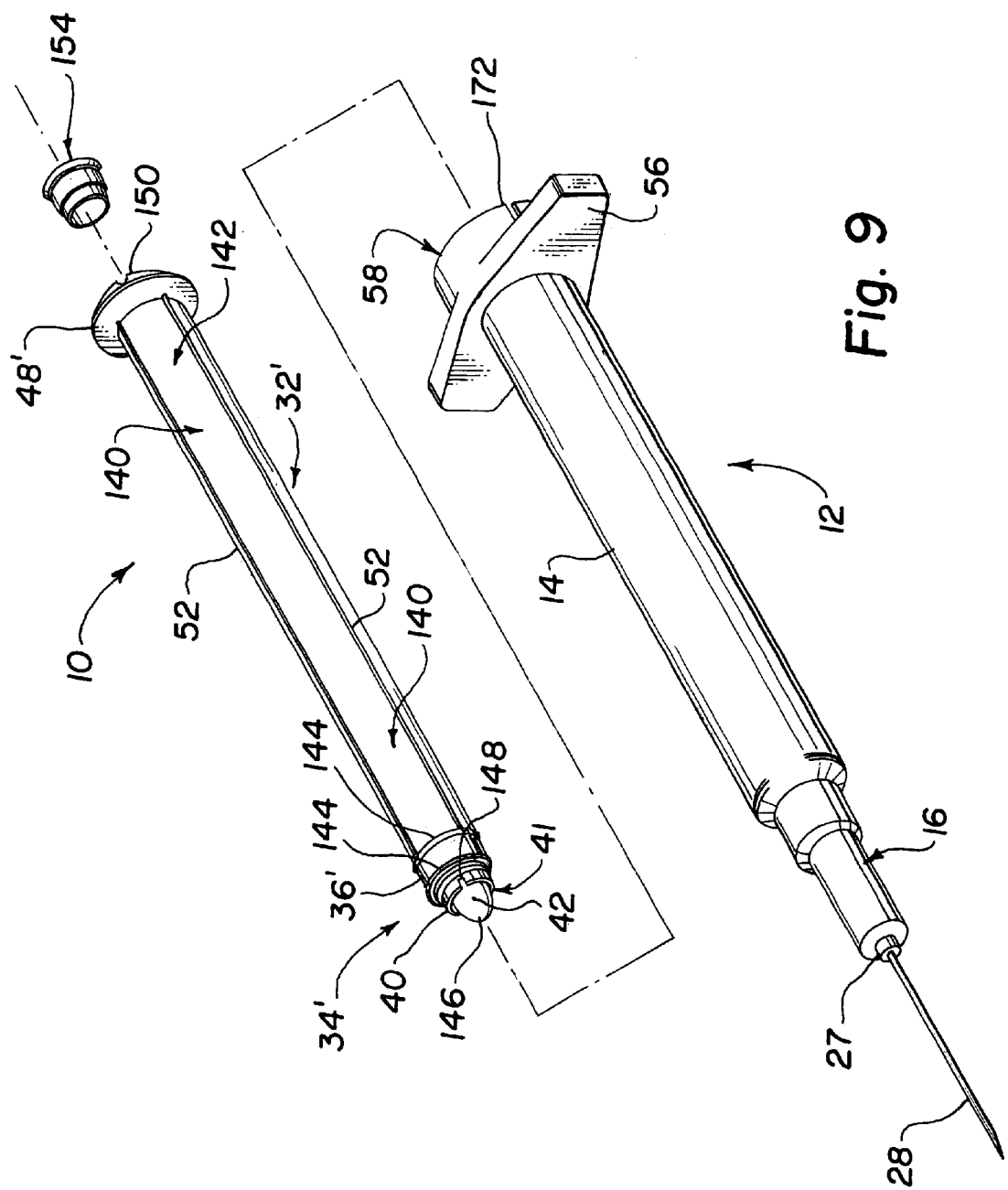
FIG. 9 is an exploded perspective view showing the barrel and retraction mechanism of FIG. 1 with a modified plunger assembly.
Figure 12:
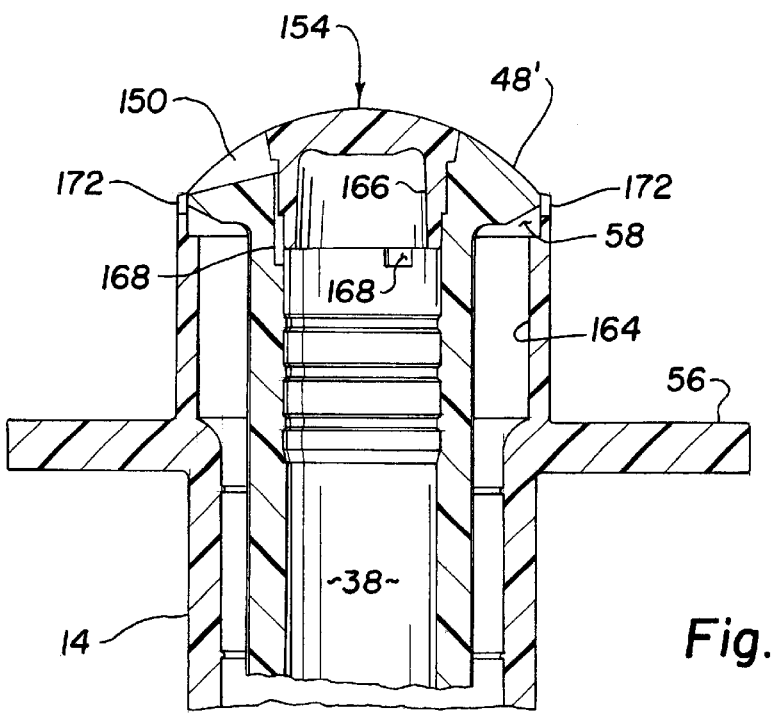
FIG. 12 is a cut away elevational view of the plunger end cap and closure of FIG. 11 as the thumb cap is just being received into the barrel opening.

Referring now to FIGS. 9 and 12, it will be noted that opening 58 in the back end of barrel 14 includes slots 172 in fluid communication with the hollow interior of the plunger through one or more channels 150 so that when thumb cap 48' is received in opening 58, no seal is created by the thumb being in contact with opening 58 which might otherwise prevent air from venting. The outer periphery of thumb cap 48' is closely received in opening 58 as the syringe is fired, to prevent reuse. Thumb cap 48' is preferably sized in relation to barrel 14 such that opening 58 is simply an extension in a linear direction of the wall of barrel 14 rather than enlarged as shown. Finally, the interior surface 164 preferably has several annular constrictions 170 designed to catch the head of stopper 42 during its rearward travel. Since stopper 42 is preferably installed from the rear of the plunger before closure 154 is put in place, the constrictions 170 must allow stopper 42 to be forced through to the front.

Figure 13:
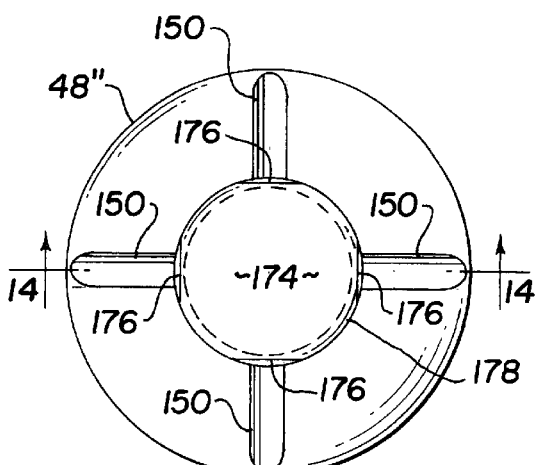
FIG. 13 is a plan view of a first alternative thumb cap and closure combination utilizing a flat sided closure and four channels in the thumb cap.
Figure 15:
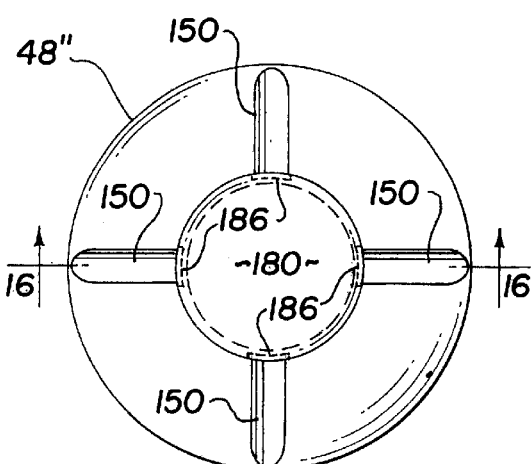
FIG. 15 is a plan view of a second alternate thumb cap and closure combination with four channels in the thumb cap and undercut portions to provide a vent passage.
Figure 14:
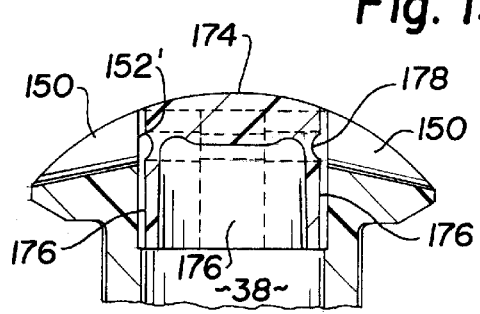
FIG. 14 is a cut away elevational view on the lines 14—14 of the thumb cap closure combination of FIG. 13.
Figure 16:
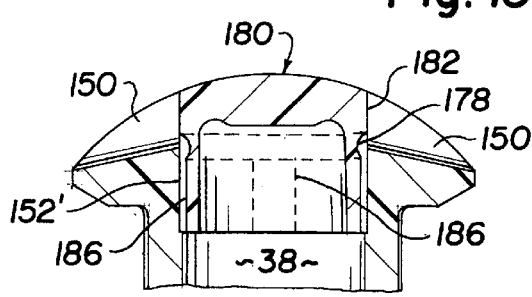
FIG. 16 is a cut away elevational view on the lines 16—16 of the combination of FIG. 16.

A first alternative thumb cap and closure arrangement is illustrated in FIGS. 13 and 14. In this embodiment, four channels 150 are provided in thumb cap 48". Closure 174 has four flat side portions 176 spaced around the periphery at 90° intervals, each in fluid communication with a channel 150. A gap is created at each flat side between the flat sides 176 and the opening 152' which are in fluid communication with interior 38 to create a flow passage for air from interior 38 through the gap along the flat side then into channel 150. Annular groove 178 in closure 174 may be used to fluidly connect each of the flat areas 176 at the level of channels 150. In addition to equalizing air flow, the annular groove allows venting of air regardless of the angular orientation of closure 174 with respect to thumb cap 48".

A second alternate embodiment has the same thumb cap 48" with a modified closure 180. Closure 180 has a head 182 which snugly fits within opening 152' which is at the back of the plunger. Opening 152' is only slightly larger than the interior of the plunger to provide a seat for the closure. Four undercut portions 186 are each in joint fluid communication with the interior 38 and one of the channels 150 to create a flow passage from the interior 38. Closure 180 effectively seals the opening 152' so that no fluid particles can escape from the opening. As in the previous embodiment, an annular groove 178 bridges each undercut portion opening into a corresponding channel 150 thereby tying the undercut portions together in fluid communication regardless of the angular orientation of the parts.

In operation, there are many advantages to the improved combination disclosed herein. The diameter of the stopper in both embodiments and the slidable retaining ring member in the first embodiment, in relation to the diameter across the fluid chamber, makes it possible to produce a syringe which withstands high blowout pressure. By minimizing the effective surface area exposed to the pressurized fluid during an injection, the syringe will withstand injection thumb force of around fifteen to eighteen pounds during injection and at the same time retract in response to as little as five to six pounds of force on the plunger once the injection fluid has been injected. Once the fluid has been injected, cumulation of force required to concurrently operate the retraction mechanism is avoided. First the stopper is moved back and then the needle holder is released. By constricting the diameter of the syringe near a transition zone where the nose begins, a constriction enables the needle holder to be smaller which in turn allows it to fit in a smaller opening with a smaller stopper in the retraction cavity of the hollow plunger.

A vacuum must be pulled in order to fill the syringe. The ring member or the needle holder, as the case may be, must seal the front nose of the syringe body because otherwise vacuum could be lost and fluid could enter the spring area and leak out the front. The hollow outer body and syringe plunger are preferably made from conventional plastic material used for syringes, which has some flexibility. The tolerances on the diameter of mating facing surfaces between the head of the needle holder and the barrel and between the stopper and head of the plunger are not critical in order to maintain a consistent holding and dislodging force. This is believed to be because increasing interference fit increases the frictional holding force only up to a point and then the surrounding wall simply expands a small amount or the internal parts are compressed a small amount without a corresponding increase in the longitudinal force required to move the retainer member or plug member in the retraction direction. It is a desirable self correcting mechanism which is a cost and quality benefit in making the parts. It is believed that a plastic retainer member could be used and the same self limiting frictional holding force would be obtained.

Figure 20:
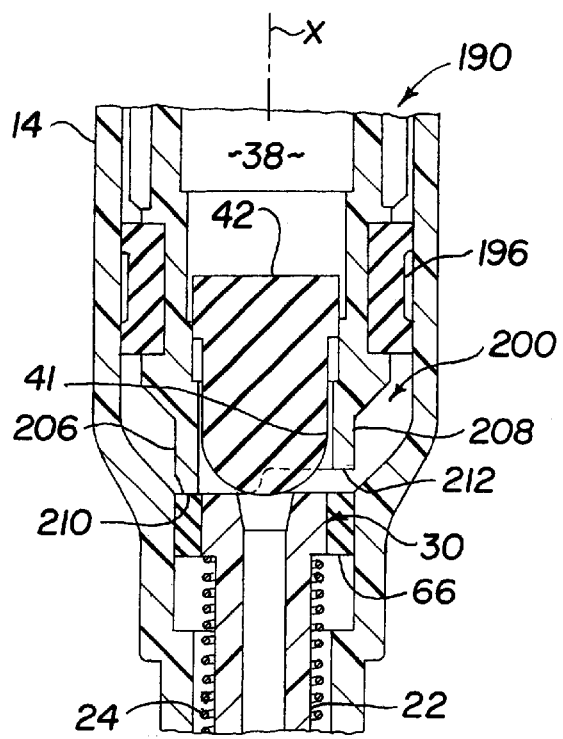
FIG. 20 is a cut away central elevation section through the modified head end of the syringe of FIG. 17 installed in the syringe body of FIGS. 1–3 or 9 showing the high part of the stepped front end in contact with a part of the transverse ring retainer holding the retractable needle.
Figure 21:
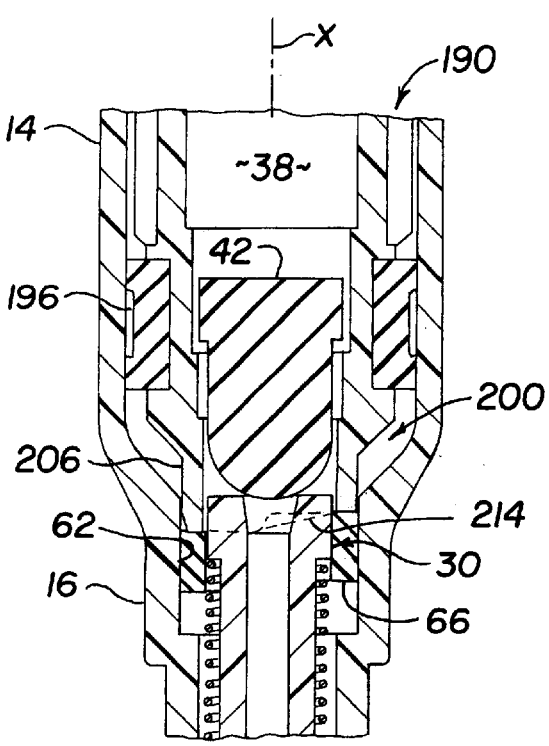
FIG. 21 is a cut away central elevation section of the structure of FIG. 20 showing in exaggerated form how the transverse retainer is tilted because of the stepped front end of the plunger as the plunger is moved forward from the position of FIG. 20.

A reduced force syringe plunger handle indicated generally by the reference numeral 190 for use in retracting a retractable syringe of the type shown in FIGS. 1–3 is illustrated in FIGS. 17, 20 and 21. Reduced force syringe plunger handle 190 is suited for use in retracting a retractable syringe of the type having an elongated hollow syringe barrel 14 having a front end portion such as nose 16 containing a retraction mechanism 20 configured for operation by forward movement of the plunger wherein the retraction mechanism has a retractable rearwardly biased needle holder 22 held by a separable retainer member or retainer 66 lodged in the front end portion 16 of barrel 14. The retainer or retainer ring 66 is a needle holding member positioned transversely at a right angle with respect to the longitudinal axis of syringe 10. The reduced force syringe plunger handle has a tubular body 192 containing flutes 52, which is reciprocatably mounted in barrel 14. The reduced force plunger has a modified head 194 upon which is mounted a plunger seal 196 for sealingly sliding in the barrel 14. Plunger seal 196 is slightly modified from the shape of seal element 36, but serves the same purpose.

Tubular body 192 is a hollow body with a wall 198 which extends forward into a tip 200 at the front of plunger handle 190. Tip 200 is configured for separating a transversely mounted retainer ring 66 from a retractable needle 28, 22 which is retracted by forward movement of the plunger at the end of an injection. It is understood that plunger 190 is completely interchangeable with plunger 32, 32 for the purpose of operating and retracting the retraction mechanism 20 of syringe 10. The only substantive difference between the plunger 32 and plunger 190 is seen at the front tip 200 where tip 200 at the front of reduced retraction force plunger 190 has a longitudinally varying front contact surface 202 configured to press first against one portion of retainer member 66 before the rest of tip 200 presses against the rest of retainer member 66. This action moves one portion of transverse retainer 66 with respect to the barrel wall and the retractable needle before the remainder of retainer 66 begins moving as the plunger 190 is moved forward. This action is believed to result in a reduction in the retraction force required to initiate and complete retraction of the retraction mechanism 20.

The longitudinally varying surface can be considered a forwardly extended portion 202 and a recessed portion 204 whereby forwardly extended portion 202 first presses against and moves part of retainer member 66 when the plunger moves forward. This constitutes a stepped front surface comprising a high step 206 and a lower step 208 with the high step 206 being the forwardly extended portion 202. Like plunger 32, plunger 190 has a wall which forms the opening 41 for a removable seal member which comprises a stopper or plug member 42. The longitudinal center line of the plunger and the syringe itself is indicated by the dotted line "X". The internal configuration of head 194 is the same as head 34 of plunger 32 as previously described.

Referring now to FIG. 20, plunger 190 is seen reciprocatably fitted in barrel 14 of syringe body 12. Here an injection has been completed and the plunger has moved forward until the high step 206 of hollow tip portion 200 comes in contact with part of the upper surface of transversely mounted retainer 66. Contact surface 210 of high step 206 is first to push against the transversely positioned retainer member 66 before the contact surface 212 of lower step 208 has been moved forward enough to touch retainer member 66. The contact surfaces 210, 212 can be considered a stepped rim around opening 41 wherein the stepped rim has a high step and a lower step. The rim preferably comprises a circular shaped wall of uniform thickness which forms the steps. As mentioned before, the effect of this structure is to apply all of the plunger force to part of the retainer ring before the plunger force is applied to the rest of the retainer thereby reducing the overall force required to move the retainer (slide it) along the inner wall of the front portion of the barrel and begin separating the retainer from the head of the needle holder in the area where it begins moving.

What happens when syringe 190 is pushed forward beyond the position of FIG. 20 is illustrated in an exaggerated fashion in FIG. 21 to illustrate the effect. Plug member 42 is pushed further back as plunger 190 moves part of the retainer member 66 which begins to slide along wall 62 of nose 16. It can be seen that this action causes retainer member 66 to tilt with respect to the axis X of the syringe. The tilting surface of the retainer member 66 is indicated by the dotted line 214. It can be appreciated that this action allows the plunger to separate one part of the retainer member from the retractable needle and move the transverse retainer relative to the front end of the barrel before the rest of the transverse retainer is separated from the retractable needle. The configuration is such that one part of the retainer must begin moving while the rest of the retainer remains stationary at some position of the plunger 190 between the positions of FIGS. 20 and 21. There is believed to be some point during this process when one side of the retainer begins. coming free of the retractable needle while the other side is still partially holding the needle.

Another version of the reduced force syringe plunger handle for use with a syringe of the type shown in FIGS. 1–3 and 9 is illustrated as plunger 190'. Plunger 190' is like plunger 32 and plunger 190 except for the modified head portion 194'. This structure is used and functions in essentially the same manner as does plunger 190 having modified plunger head 194. Tubular body 192 of FIGS. 18 and 19 is a hollow body with a wall 198 which extends forward into a tip 216 at the front of plunger handle 190'. Tip 216 is configured for separating a transversely mounted retainer ring 66 from a retractable needle 22, 28 which is retracted by forward movement of the plunger at the end of an injection cycle. The only substantive difference between plunger 32 and plunger 190' is seen at front tip 216 where tip 216 has a longitudinally varying front surface configured to press first against one portion of transverse retainer member 66 before pressing against the rest of retainer member 66. The longitudinally varying surface can be considered a forwardly extending portion 218 which in this case is transverse surface lying in a plane perpendicular to the longitudinal axis X of the syringe. The remainder of the contact surface at the front of syringe 190' is an angled surface 220 which is formed in the rim 222 at the front tip 216 of syringe 190'. Angled surface 220 is angled from the longitudinal center line of the syringe and with respect to the flat surface 218. It is formed as if the transverse tip at the front end syringe plunger 32 were partially cut off at an angle to its long axis. Rim 222 is preferably a circular wall of uniform thickness. The rim 222 defines the opening 41 which is shown in FIG. 19 as containing the removable seal member comprising a stopper or plug member 42. The internal configuration of head 194' is the same as head 34 of plunger 32 as previously described. When used in a syringe of FIGS. 1–3, the flat portion 218 on tip 216 presses against and moves the transverse retainer member 66 first when the plunger moves forward to retract the syringe before the angled surface 220 begins pushing on the other side of the retainer ring 66 thereby moving it and separating it from the retractable needle.

Figure 22:
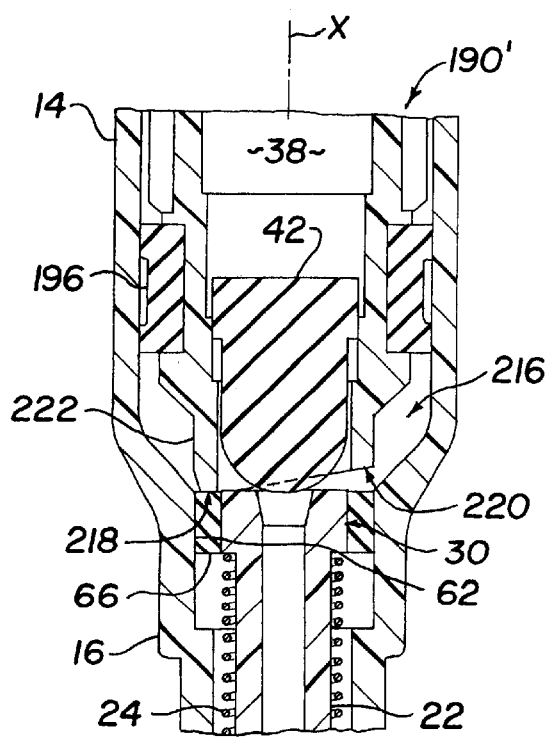
FIG. 22 is a cut away central elevation section through the modified head of the plunger of FIG. 19 corresponding to the view shown in FIG. 20 wherein the high or longest part of the angled front edge at the tip of the plunger is just coming in contact with one part of the transverse retainer at the end of an injection.
Figure 23:
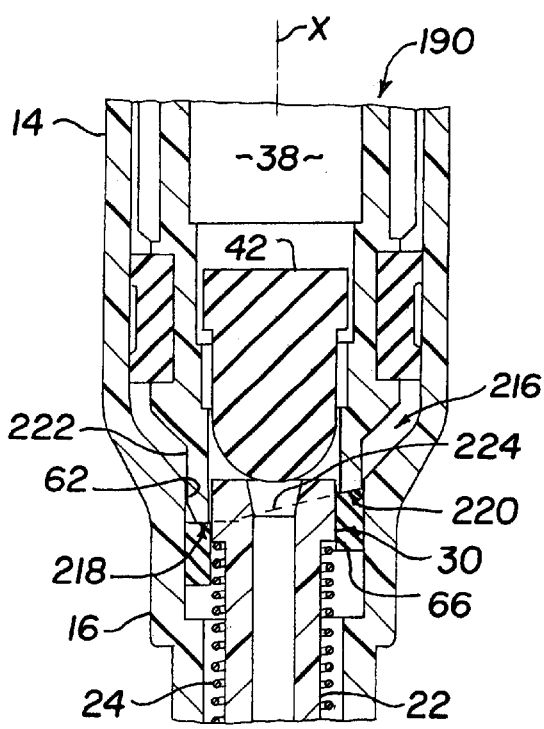
FIG. 23 is a cut away central elevation section through the structure of FIG. 22 showing in greatly exaggerated form how the transverse retainer is tilted as the plunger moves forward from the position of FIG. 22 whereby one part of the retainer ring is moved before the rest of the retainer ring is moved.

Referring now to FIGS. 22 and 23, plunger 190' is seen fitted in barrel 14 of syringe body 12. In FIG. 22, an injection has been completed and the plunger is moved forward until the relatively flat portion 218 of rim 222 comes into contact with part of transverse retainer 66. FIG. 23 shows the position of retraction parts just as the plunger has been moved forward at the end of the injection. Flat portion 218 of tip 216 begins moving part of transverse retainer 66 with respect to the wall 62 of the front of barrel 14 before angled contact surface 220 comes in to forceful contact with the remainder of retainer 66.

FIG. 23 shows the position of the plunger and retractable parts in an exaggerated fashion as plunger 190 has been pushed forward from the position of FIG. 22. Plug member 42 is pushed further back as plunger 190' moves one part of transverse retainer 66 which begins to slide along the inner wall at the front of the barrel comprising nose 16 before the other part of retainer 66 is moved. It can be seen that this action causes retainer member 66 to tilt (exaggerated) with respect to the axis X of the syringe. The exaggeratedly tilted surface of retainer member 66 is illustrated by the dotted line 224. The action is similar to that of the tip structure of FIG. 17 in that the irregularly shaped front edge of the plunger 190' allows the plunger to begin to move and separate one part of transverse retainer 66 with respect to the surface of the barrel and the head of the retractable needle before the rest of the transverse retainer is moved by the angled surface 220. This condition would occur at some forward position of the plunger intermediate the position shown in FIGS. 22 and 23.

Figure 24:
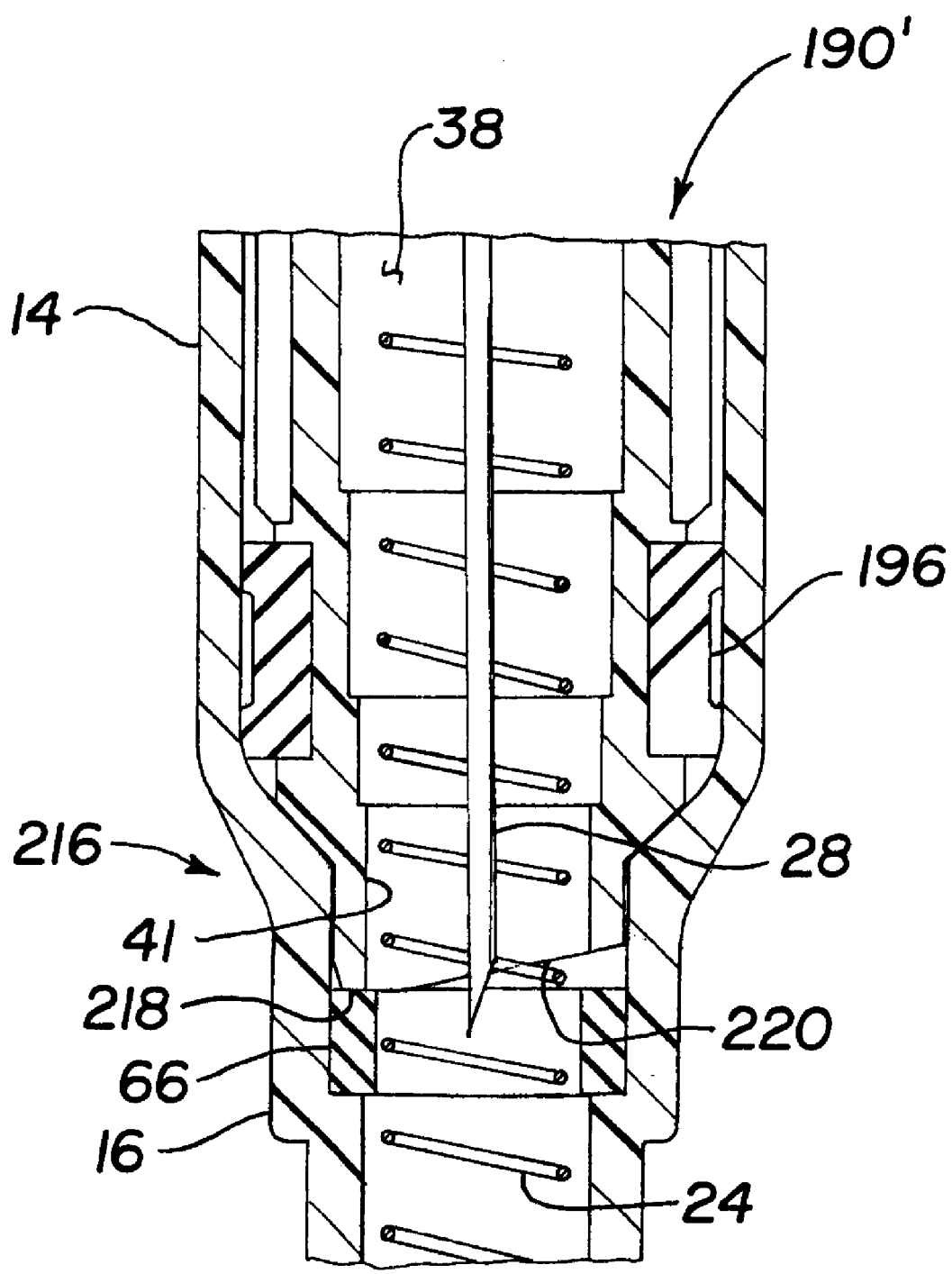
FIG. 24 is a cut away central elevation section of the structure of FIGS. 22 and 23 after the reduced force plunger handle is pushed forward beyond the position of FIG. 23 causing retraction to occur.
Figure 25:
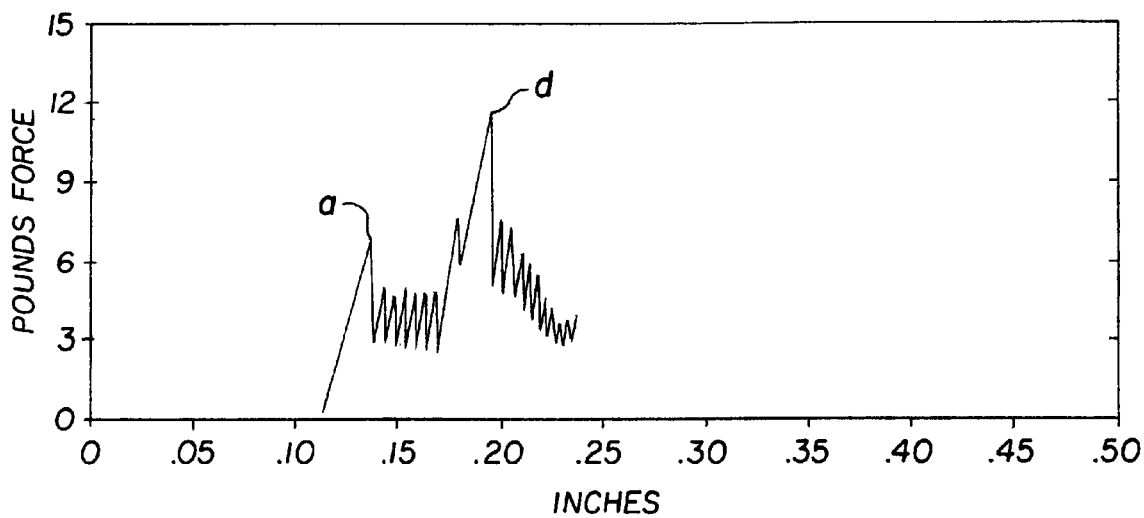
FIG. 25 is a graph illustrating axial plunger forces during retraction of the unmodified standard syringe plunger shown in FIGS. 1–3 and 9 wherein the hollow front end of the plunger is transverse and perpendicular to the long axis of the syringe.

FIG. 24 shows the fully retracted position of the syringe 10 with the modified reduced force syringe plunger 190' after it has been fully depressed. The retainer member 66 is shown in a transverse position but it would not necessarily have to be in a transverse position after the retraction has been completed. It could be slightly tilted in the final retraction position of FIG. 24 without harming the retraction process.

We believe surprising results are demonstrated in a series of tests based upon samples of 30 prototype syringes in Table 1 below, which are designated "Control Group", "Stepped Plunger" and "Sloped Plunger". The control group is actually the production syringe which is essentially the same as the syringe disclosed, in FIGS. 1–3 and 9. Although the control group plungers have some small slots in the rim at the front edge of the tip to allow fluid to pass laterally, the front edge (rim) is square and at right angles to the main long axis of the syringe as shown in FIG. 1. The stepped plunger and the sloped plunger were tested in the same barrel design of the control group, which is the production barrel and retraction mechanism essentially the same as FIG. 1. The plungers were modified by altering only the tip into a step or a slope without changing anything else except for a slightly different outer plunger seal 196. The retraction mechanism in all three sets of tests remained exactly the same.

The syringes were tested in a United Tensile Tester Model SSTN-1 using a 100 pound load cell on the tester and a test speed of one inch per minute. The syringe was placed in a fixture with the needle downward and the block which is connected to the load cell was moved downward to rest upon the plunger handle thumb cap and moved forward to determine the functionality force. The functionality or functionality force is defined as the highest load force measured during the forward movement of the plunger until retraction occurred. It includes the force required to move the seal comprising the stopper or plug 42 in the central opening 41 of the plunger as well as the plunger force required to accomplish the retraction of the retractable needle by moving the retainer ring forward. Functionality is the highest peak in the force graphs in FIGS. 25–28 which will be discussed later. Table 1 includes the average plunger force, maximum plunger force, minimum plunger force, and standard deviation (Stdev) for each group of data. This data for the sloped plunger is based upon 29 samples due to one bad data point. Functionality is rounded to the nearest 1/10 pound.

TABLE 1

| Control Group | | Stepped Plunger | | Sloped Plunger | |
| --- | --- | --- | --- | --- | --- |
| Sample # | Functionality | Sample # | Functionality | Sample # | Functionality (lbs) |
| 1 | 10.5 | 1 | 6.7 | 1 | 8.7 |
| 2 | 9.1 | 2 | 7.2 | 2 | 7.4 |
| 3 | 9.1 | 3 | 6.2 | 3 | 6.8 |
| 4 | 13.7 | 4 | 7.4 | 4 | 7.4 |
| 5 | 11.9 | 5 | 10.4 | 5 | 8.1 |
| 6 | 11.5 | 6 | 6.4 | 6 | 8.4 |
| 7 | 7.6 | 7 | 6.3 | 7 | 7.6 |
| 8 | 12.7 | 8 | 6.9 | 8 | 7.2 |
| 9 | 10.8 | 9 | 6.6 | 9 | 8.8 |
| 10 | 11.8 | 10 | 6.7 | 10 | 8.2 |
| 11 | 8.9 | 11 | 6.7 | 11 | 7.4 |
| 12 | 10.4 | 12 | 6.5 | 12 | 7.1 |
| 13 | 11.1 | 13 | 6.4 | 13 | 7.6 |
| 14 | 9.1 | 14 | 6.3 | 14 | 8.8 |
| 15 | 10.5 | 15 | 7.7 | 15 | 7.3 |
| 16 | 10.7 | 16 | 7.4 | 16 | 9.3 |
| 17 | 8.8 | 17 | 6.6 | 17 | 7.1 |
| 18 | 9.3 | 18 | 6.7 | 18 | 7.7 |
| 19 | 9.7 | 19 | 5.6 | 19 | 8.3 |
| 20 | 9.8 | 20 | 7.0 | 20 | 7.7 |
| 21 | 12.4 | 21 | 7.4 | 21 | 8.2 |
| 22 | 10.9 | 22 | 6.4 | 22 | 7.6 |
| 23 | 10.5 | 23 | 6.9 | 23 | 7.2 |
| 24 | 9.1 | 24 | 7.3 | 24 | 7.6 |
| 25 | 10.3 | 25 | 7.3 | 25 | 9.2 |
| 26 | 12.9 | 26 | 6.7 | 26 | 7.2 |
| 27 | 14.9 | 27 | 7.2 | 27 | Bad Data |
| 28 | 8.9 | 28 | 7.6 | 28 | 8.3 |
| 29 | 11.1 | 29 | 6.4 | 29 | 8.0 |
| 30 | 7.6 | 30 | 7.8 | 30 | 7.1 |
| Min | 7.6 | Min | 5.6 | Min | 6.8 |
| Max | 14.9 | Max | 10.4 | Max | 9.3 |
| Average | 10.5 | Average | 7.0 | Average | 7.8 |
| Stdev | 1.7 | Stdev | 0.8 | Stdev | 0.7 |
| Range | 7.3 | Range | 4.8 | Range | 2.5 |

A very substantial reduction in the average plunger retraction force functionality is indicated by the average of the 30 tests. The control group showed an average of 10.5 pounds plunger force as compared to only 7 pounds for the stepped plunger of FIG. 17. This is roughly a 30% reduction in the average plunger retraction force. Moreover, although there are a few anomalous test results, variation and range of the functionality force was also less with the stepped plunger of FIG. 17 and the sloped plunger of FIG. 19 than with the control group. Although the sloped plunger had a slightly higher average plunger functionality force, it was still very substantially lower than the control group.

FIGS. 25–28 are graphical representations of some examples taken out of Table 1. These graphs all follow the same pattern. They measure the functionality force on the plunger as the plunger moves from its end of injection position of FIG. 1 over a relatively short period of plunger forward displacement until retraction occurs. Because the seal member 42 extends slightly beyond the front tip of the plunger, it starts to slide rearwardly with respect to the plunger before the front edge of the plunger tip contacts retainer 66. This part of the curve is exemplified by the first peak which is identified as "a" in FIGS. 25, 26 and 28. The peak denominated "d" is automatically placed on the highest peak by the testing machine. This is irrespective whether it is a first or second peak.

In the control group of example 25, the peak "a" represents the initial force required to first move the plug member 42 and the second peak "d" represents the force required to initiate movement of the transverse retainer 66 with the standard plunger of FIGS. 1–3. Although there are some lower values in the group, some 18 of the 30 samples have a functionality force of 10 pounds or more. The plunger force first required to move the retainer ring with respect to the walls of the barrel and the retractable needle is substantially more than the force required to move the plug back into the plunger. In this example it is nearly twice as much.

Figure 26:
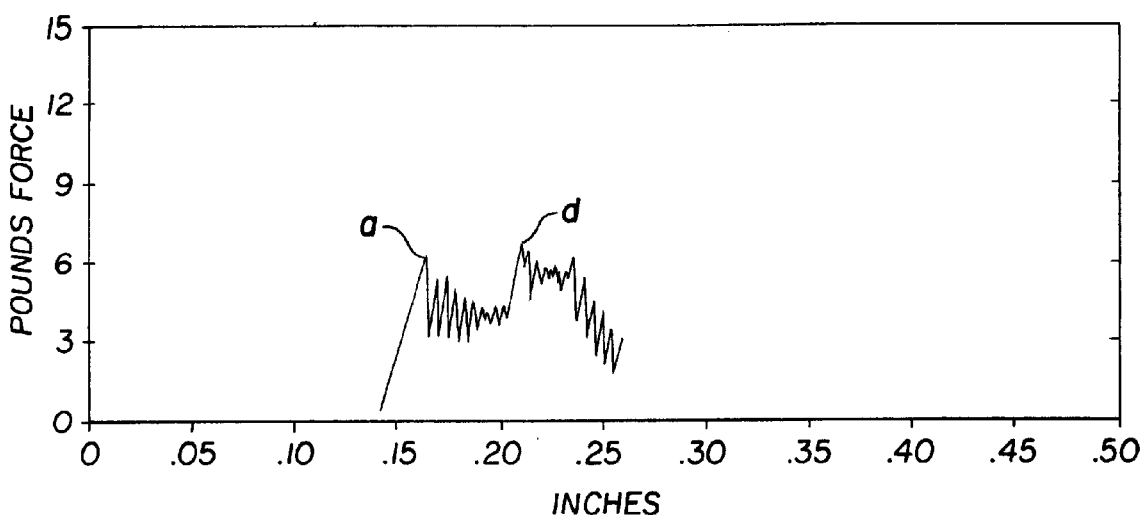
FIG. 26 is a graph similar to FIG. 25 showing the plunger retraction forces on the syringe shown in FIGS. 1–3 using the stepped front reduced force syringe plunger handle of FIG. 17.
Figure 27:
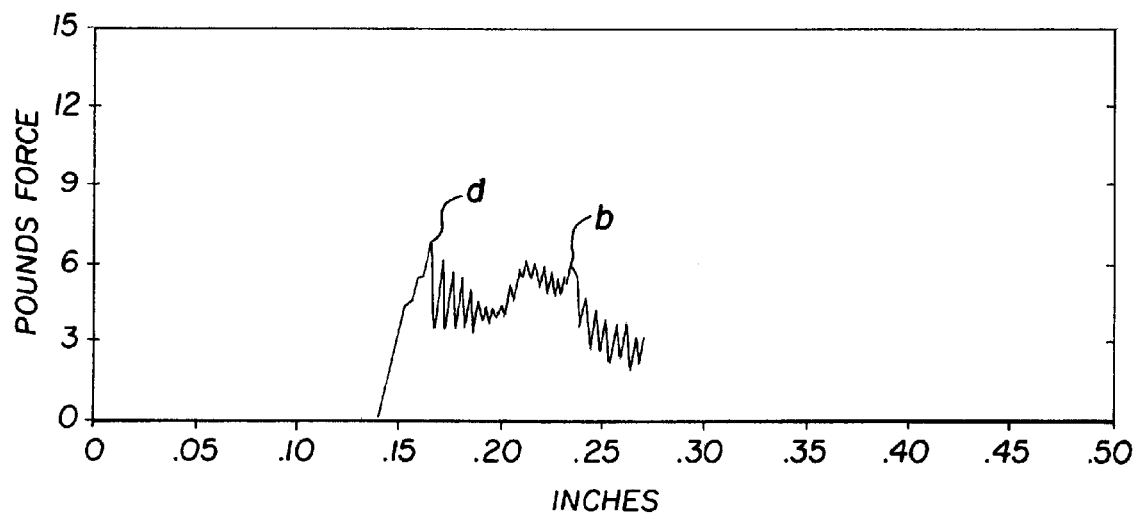
FIG. 27 is another example of a graph illustrating plunger retraction forces in the syringe of FIGS. 1–3 when using the stepped front reduced force syringe plunger handle of FIG. 17.

FIGS. 26 and 27 represent two examples of the stepped plunger with a substantially lower peak force required to move the retainer member 66 denominated at point "d" in FIG. 26 and point "b" in FIG. 27. In fact, in FIG. 27 the plunger force is actually less than the initial force required to move the stopper 42 which the machine identified as the first peak "d". The reduction in plunger force associated with the second peak, i.e. movement of the transverse retainer, suggests that the plunger force required to move the ring member during retraction using the stepped plunger is now nearly the same as the lower force required to remove the sealing stopper 42. Based on the graphs of FIGS. 25–28, it appears the force required to remove the stopper never rises above about 7 pounds.

Figure 28:
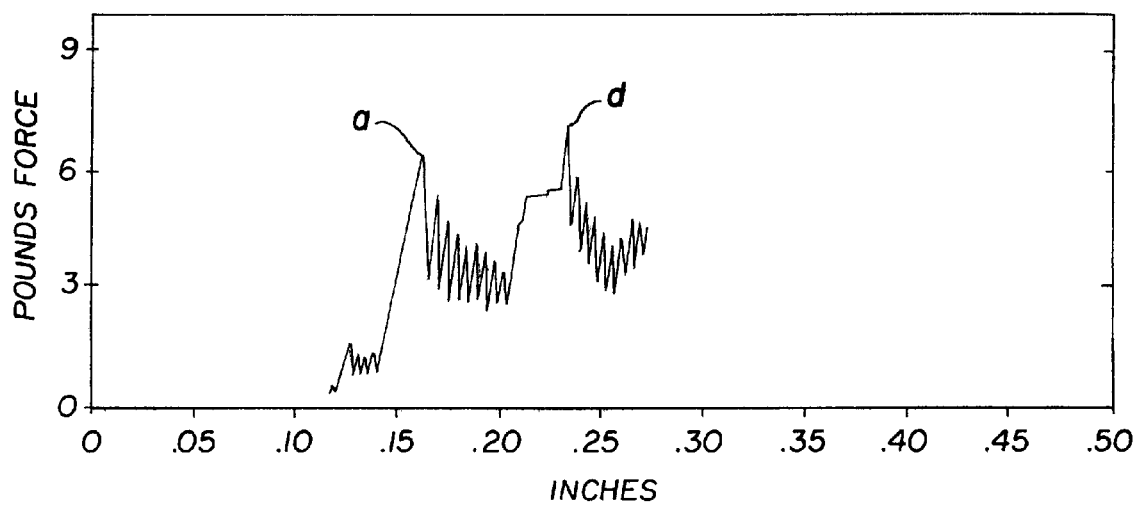
FIG. 28 is an exemplary graph of the plunger forces during retraction of the syringe of FIGS. 1–3 utilizing the angled front reduced force syringe plunger handle as illustrated in FIG. 19.

FIG. 28 which represents the slopped plunger is plotted on a larger force scale than the other graphs. FIG. 28 illustrates a first peak "a" for removal of the stopper and the second peak "d" where the retainer is being moved. This graph is quite similar to the results using the stepped plunger tip, although average plunger force is slightly higher than the results obtained with the stepped plunger in FIGS. 26 and 27. The identity of the graphs is given in the following table:

TABLE 2

| FIG. | Test Group | Sample # | Functionality |
|---|---|---|---|
| 25 | Control Group | 6 | 11.5 |
| 26 | Stepped Plunger | 9 | 6.6 |
| 27 | Stepped Plunger | 18 | 6.7 |
| 28 | Sloped Plunger | 12, 17 or 30 | 7.1 |

The significance of this improvement cannot be over estimated. In the superior syringe design of FIGS. 1–3 and 9, the retaining ring member 66 frictionally holds the head of the needle holder in opposition to the biasing force applied by the spring. In addition, it is frictionally supported at the inner wall of the barrel and is subject to forces imposed on the needle by the act of puncturing rubber seals on vials on the retainer and by blow out pressure as mentioned in the specification. Therefore, it is difficult to achieve reliability and avoid premature retractions unless these frictional holding forces are high enough to withstand these imposed forces. There must be a certain amount of frictional force imposed on the retractable parts which must be overcome by the plunger force during retraction. This makes it difficult to reduced the amount of plunger force required to retract the syringe below a certain amount.

The beauty of the present invention is that a way has been found to reduce the force on the plunger required to retract the syringe without making any changes whatsoever to the retraction mechanism itself. All of the design features and characteristics that prevent the problem of premature retraction by forces imposed on the needle and retainer ring remain effective, but the plunger retraction force is desirably reduced to a lower level and made more uniform and reliable when the modified plunger tips are used.

In the best mode, it is believed that the stepped plunger tip is preferable to the sloped plunger although the exact shape and dimensions have not been optimized. It is clear that the basic principle of configuring the tip to apply all of the plunger force to one part of the retainer ring before the plunger force is applied to the rest of the retainer ring is a fundamental principle regardless of the specific shape of the tip. The high step on the stepped plunger preferably represents about half of the area of the rim at the tip. The samples in Table 1 of FIGS. 25–28 are based on a 3 cc syringe wherein the opening 41 has a diameter of about 0.18 inches. The length of the high step in the axial direction is about 0.030 inches more than the low step of the FIG. 17 embodiment although the actual dimensions may vary because the prototypes were prepared by hand.

It is believed that a step of about 10–30 thousandths of an inch is appropriate depending upon the diameter of the tip. It is believed that the step has to be higher for a syringe of a greater diameter and lower for a syringe with a smaller diameter tip. The sloped plunger is believed to have about a 5 degree angle on the angled portion 220 of the surface while the flat portion 218 represents an area of about 13% of the area of the rim 222. If the step or the slope is too great as compared to the diameter of the tip, it would be possible to get a locking effect that could actually increase the friction to remove the retainer member and possibly result in an inconsistent retraction. Some experimentation would be required to find the best combination of dimensions.

These factors may also be affected by the resiliency of the retainer member, the height of the retainer relative to the retractable needle on which it is mounted, and other factors. Although two preferred embodiments of the tip shape have been disclosed, it should be understood that other variations in shape including more or less step or slope and more or less initial contact area between the tip and the retainer, are within the scope of the invention as long as the force applied by the plunger is not uniformly placed upon the retainer, and allows some tilting of the retainer to occur during forward motion of the plunger.

In the best mode the stopper and the ring member are preferably made from a thermoplastic rubber material designated number 181-55 available from Advanced Elastomer Systems, 540 Maryville Central Drive, St. Louis, Mo. and sold under the trade name Santoprene®. It is said to have a characteristic hardness around 55 on the Shore A durometer scale which allows for the right amount of resistance to compression, fluid resistance such that the material does not swell when in contact with most fluids, environmental stability allowing the friction and sealing properties to remain non-temperature sensitive, good property retention after aging and excellent property retention after sterilization by all accepted methods. The plunger seal around the head of the plunger is conventional.

The parts are few in number and easily mass produced. The alternate embodiment has the fewest number of separate parts of any tamperproof retractable syringe. The plunger has a one piece hollow outer body with a transition zone and a narrow nose portion. The internal diameter is stepped to greater diameters from front to back for molding around a non-collapsible core which can be extracted from the rear. The same is true for the plunger.

Assembly is greatly simplified and can be accomplished with high speed mechanized equipment. The needle holder and spring are installable from the rear of the barrel without the needle. In the first embodiment the retainer member is forced fit over the inner head of the needle holder and the assembly together with the uncompressed spring are pushed forward and held by sliding engagement of the cooperating inwardly and outwardly facing surfaces while compressing the spring. The front of the needle holder passes through an opening in the nose which makes it easy to install the needle from the front by conventional means. The alternate embodiment is installed the same way except that there is no separable retainer member around the head of the needle holder.

The narrow nose provides a particular advantage for mechanized assembly. The nose has a wall defining an elongated internal cavity which closely confines the spring and needle holder combination. During installation this cavity serves as a guide to steer the needle holder and uncompressed spring into a compressed state of the spring. This solves an important assembly problem. If there is much lateral space in the nose around the spring, when the uncompressed spring is being compressed, it is a laterally unstable column which flexes sideways and bunches up causing a jam up. It might be added that rounded edges on the bottom of the slot directly below retainer 66 would further facilitate entry of the end of the spring.

The stopper is also installable from the rear of the plunger by pushing it forward until the cooperating lands are slidingly engaged. Then plug member 50 is force fit or otherwise fixed in the opening at the back of the plunger and the plunger is installed in the outer body. It is not necessary to try to pass the sharp needle through an elongated body with constricted openings where slight misalignment could cause hangups. The head of the needle holder simultaneously acts as a seal as well as a holding device such that no seal is required at the tip of the nose and no ultrasonic welding of separate parts is required.

There is no necessity for using internal locking teeth of any kind. No locking teeth are needed to hold the retraction mechanism or to lock the plunger after retraction. Locking teeth present difficult molding and quality control problems, tend to be temperature sensitive and tend to require a larger diameter barrel which increases premature blowout problems. In addition to the non-reusability provided by separation of the retainer ring from the head of the needle holder and dislodgement of the stopper, the plunger is not accessible after retraction because it is depressed within an opening at the back of the outer body. This additional tamperproof feature is provided in a one piece body without the necessity for hooking anything or twisting any thing. The easily made and installed force fit plug at the back of the retraction cavity prevents access to the retracted components.

We claim:

1. A reduced force syringe plunger handle for use in retracting a retractable syringe of the type having an elongated hollow syringe barrel having a front end portion containing a retraction mechanism activated by forward movement of the plunger relative to the barrel, the retraction mechanism comprising a rearwardly biased needle holder held by a separable retainer member lodged in the front end portion of the barrel, the retainer member having first and second sides oppositely disposed relative to a longitudinal axis through the barrel, the syringe plunger handle having a tubular body reciprocatably mounted in the barrel, the tubular body having a head comprising a front tip configured to contact and separate the retainer member from the needle holder by forward movement of the plunger relative to the barrel thereby releasing the needle holder for retraction, wherein the improvement comprises:

the front tip of the plunger having a longitudinally varying front surface comprising a first forwardly extending side configured to contact and move the first side of the retainer member relative to the needle holder and the barrel, and a second forwardly extending side disposed rearwardly of the first forwardly extending side, the second forwardly extending side configured to thereafter contact and move the second side of the retainer member relative to the needle holder and the barrel when the plunger is moved forwardly relative to the barrel, thereby reducing the plunger force required to activate the retraction mechanism.

2. The reduced force syringe plunger handle of claim 1 wherein the longitudinal varying front surface is longitudinally stepped relative to the longitudinal axis through the barrel.

3. The reduced force syringe plunger handle of claim 1 wherein a substantial portion of the longitudinally varying front surface is angled relative to the longitudinal axis through the barrel.

4. The reduced force syringe plunger handle of claim 3 wherein the longitudinally varying front surface includes a relatively flat portion which contacts the first side of the retainer member when the plunger moves forward relative to the barrel to retract the syringe.

5. The reduced force syringe plunger handle of claim 1 wherein a releasable plug member is lodged in the front tip of the syringe plunger, the plug member being exposed more on one side than on the other side because of the longitudinally varying front surface.

6. The reduced force syringe plunger handle of claim 5 wherein the releasable plug member has a portion which extends forward beyond the front tip of the plunger.

7. The reduced force syringe plunger handle of claim 1 wherein the first forwardly extending side of the longitudinally varying front surface tilts the retainer member relative to the needle holder and barrel prior to being contacted and moved by the second forwardly extending side.

8. A reduced force syringe plunger handle for use in retracting a retractable syringe having a long axis and a transversely positioned retainer member in a retraction mechanism having a retractable needle, comprising:

an elongated tubular syringe plunger having an end cap for depression of the plunger at a back end and a head portion at a front end of the plunger, the head portion having a plunger seal for sealingly slidingly in a syringe barrel;

the syringe plunger having a tubular wall containing a retraction cavity within the syringe plunger, the tubular wall extending forwardly into the head portion;

the head portion having a forwardly extending hollow tip portion defining an opening through the tip portion leading into the retraction cavity;

the hollow tip portion having a contact surface at the front of the plunger which varies axially in forward extension at different angular locations with respect to said opening, wherein one portion of the contact surface is configured to push first against the transversely positioned retainer member before the rest of the contact surface engages the retainer member thereby tilting the retainer member during retraction of the retractable needle;

whereby the plunger force required for release of the retainer member from the retractable needle is reduced as compared to a plunger having a generally transverse contact surface and the same retainer member and retraction mechanism.

9. The reduced force plunger handle of claim 8, wherein said contact surface comprises a stepped rim around said opening, the stepped rim having a high step and a lower step wherein the high step is first to push against the transverse retainer member.

10. The reduced force plunger handle of claim 9, wherein the high step portion of the stepped rim is roughly half of the total stepped rim configuration.

11. The reduced force plunger handle of claim 9, wherein the high step portion of the stepped rim extends for more than about one quarter of the total stepped rim configuration.

12. The reduced force plunger handle of claim 9, whereas the hollow tip portion defining said opening is of a reduced diameter as compared to the tubular syringe plunger.

13. The reduced force plunger handle of claim 8, wherein the opening through the tip portion leading into the retraction cavity has a removable seal.

14. The reduced force plunger handle of claim 13, wherein the opening through the tip portion leading into the retraction cavity is sealed with a releasable plug member that is lodged in the tip portion of the syringe plunger wherein a portion of the plug member extends forwardly beyond the high step portion of the stepped rim.

15. The reduced force plunger handle of claim 8, wherein a releasable plug member is lodged in the tip of the syringe plunger, the plug member being exposed more on one side where the lower step is located and exposed less where the higher step is located.

16. The reduced force plunger handle of claim 8, wherein the contact surface at the front of the plunger is substantially an angled surface with respect to the long axis of the syringe such that one portion of the angled contact surface presses against the retainer member when the plunger moves forward before the remainder of the angled surface presses against the retainer member.

17. The reduced force plunger handle of claim 8, wherein the contact surface at the front of the plunger has a relatively flat transverse portion and an angled portion with respect to said long axis, said relatively flat transverse portion being the part of said contact surface which presses first against the retainer member when the plunger moves forward.

18. A method of reducing plunger retraction force in a retractable syringe of the type having a barrel, a syringe plunger which reciprocates axially in the barrel and a front mounted retraction mechanism in the barrel having a retractable needle being held in position in the barrel by means of a transverse retainer which is separated from the retractable needle by contact between the front tip portion of the plunger and the transverse retainer when the plunger is moved forward after an injection to push the retainer off the retractable needle and allow retraction, comprising the step of:
   providing a plunger having a front edge on the front tip portion configured to push on one portion of the retainer before pushing on the rest of the retainer when the plunger is pushed forward at the end of an injection;
   pushing the plunger forward to bring the front edge of the tip portion in contact with the transverse retainer member; and
   tilting the transverse retainer with respect to the retractable needle while it is being separated from the retractable needle by forward movement of the plunger.

19. The method of claim 18 wherein the step of tilting the transverse retainer member with respect to the retractable needle while it is being separated from the retractable needle by forward movement of the plunger includes the step of separating one part of the transverse retainer member from the retractable needle before the rest of the transverse retainer is separated from the retractable needle.

20. The method of claim 18 wherein the plunger is configured with a front edge comprising an opening and a stepped rim around said opening having a high step and a lower step wherein the step of pushing the plunger forward comprises the step of bringing the high step into first contact with the transverse retainer before the lower step contacts the transverse retainer.

21. The method of claim 20 wherein the step of providing a plunger includes a releasable plug lodged in said opening and wherein the step of pushing the plunger forward to bring the front edge of the front tip portion in contact with the transverse retainer member is preceded by the step of moving said plug member.

22. The method of claim 18 wherein the plunger is configured with a hollow front tip portion having an angled opening leading into a hollow portion of the syringe plunger and the step of pushing the plunger forward comprises the step of bringing the forwardmost part of the front edge into first contact with the transverse retainer thereby tilting the transverse retainer with respect to the retractable needle while it is being separated from the retractable needle by forward movement of the plunger.

23. The method of claim 22 wherein the step of providing a plunger includes a releasable plug lodged in said opening and wherein the step of pushing the plunger forward to bring the forwardmost part of the front tip portion in contact with the transverse retainer member is preceded by the step of moving said plug member.

24. A method of reducing plunger retraction force in a retractable syringe of the type having a barrel, a syringe plunger which reciprocates axially in the barrel, and a front mounted retraction mechanism in the barrel having a retractable needle being held in position by means of a transverse retainer with an outside edge in contact with the inside surface of the front of the barrel wherein the transverse retainer is separable from the retractable needle upon forward movement of the plunger after an injection is made whereby a front tip portion of the plunger pushing against the retainer moves the retainer forward in the front of the barrel thereby freeing the retractable needle, comprising the steps of:
   providing a plunger having a front edge on the front tip portion configured to slide one portion of the outer edge of the transverse retainer with respect to the front of the barrel before beginning to move the rest of the retainer with respect to the front of the barrel when the plunger is pushed forward at the end of an injection; and
   pushing the plunger forward to bring the front edge of the tip portion in contact with the transverse retainer member; and
   moving one portion of the transverse retainer with respect to the front of the barrel before moving the rest of the transverse retainer during forward movement of the plunger while the retractable needle is being separated from the transverse retainer.

25. The method of claim 24 wherein the steps of providing a plunger, bringing the front edge of the tip portion in contact with the transverse retainer member and moving one part of the transverse retainer member with respect to the front of the barrel before the remainder of the transverse retainer begins moving include the step of contacting the transverse retainer with the front edge of the plunger comprising an opening and a stepped rim around said opening having a high step and an lower step wherein the step of pushing the plunger forward comprises the step of bringing the high step into first contact with the transverse retainer before the lower step comes into contact with the transverse retainer.

26. The method of claim 24 wherein the step of providing a plunger includes providing a plunger having and opening in the tip portion and a releasable plug member lodged in said opening of the syringe plunger and the step of pushing the plunger forward to bring the front edge of the tip portion in contact with the transverse retainer member is preceded by the step of moving said plug member.

27. The method of claim 24 wherein the plunger is configured with a front edge comprising substantially an angled surface with respect to the long axis of the syringe such that one portion of the angled contact surface pushes first against one part of the transverse retainer member when the plunger is pushed forward and thereby begins separating the transverse retainer from the retractable needle by sliding one part of the transverse retainer with respect to the front of the barrel before the remainder of the transverse retainer begins sliding with respect to the barrel.

28. The method of claim 27 wherein the step of providing a plunger includes the step of providing an angled contact surface which includes a relatively flat transverse portion and an angled portion with respect to the long axis of the syringe wherein the relatively flat transverse portion is the portion which first contacts the transverse retainer and first moves a part of the transverse retainer with respect to the front of the barrel before the rest of the transverse retainer is moved.

* * * * *

UNITED STATES PATENT AND TRADEMARK OFFICE
CERTIFICATE OF CORRECTION

PATENT NO. : 6,572,584 B1
DATED : June 3, 2003
INVENTOR(S) : Thomas J. Shaw, Judy Zhu and Diane Rutherford It is certified that error appears in the above-identified patent and that said Letters Patent is hereby corrected as shown below:

Column 3,
Line 53, replace "with" with -- which --.

Column 9,
Line 48, replace "impossible," with -- impossible --.

Column 12,
Line 17, replace "66 a" with -- 66a --.

Column 13,
Line 34, replace "exceed" with -- exceeds --.

Column 18,
Line 57, replace "32, 32" with -- 32, 32' --.

Column 19,
Line 57, replace "begins," with -- begins --.

Column 20,
Line 42, replace "190" with -- 190' --.

Column 25,
Line 18, replace "any thing" with -- anything --.

Column 26,
Line 16, replace "sealingly slidingly" with -- sealingly sliding --.

Signed and Sealed this

Seventh Day of October, 2003

JAMES E. ROGAN
*Director of the United States Patent and Trademark Office*